(12) United States Patent
Drew

(10) Patent No.: US 12,016,949 B2
(45) Date of Patent: Jun. 25, 2024

(54) VIRUS

(71) Applicant: iosBio Ltd, Haywards Heath (GB)

(72) Inventor: Jeffrey Drew, West Sussex (GB)

(73) Assignee: iosBio Ltd, Haywards Heath (GB)

( * ) Notice: Subject to any disclaimer, the term of this patent is extended or adjusted under 35 U.S.C. 154(b) by 886 days.

(21) Appl. No.: 16/475,417

(22) PCT Filed: Jan. 5, 2018

(86) PCT No.: PCT/GB2018/050021
§ 371 (c)(1),
(2) Date: Jul. 2, 2019

(87) PCT Pub. No.: WO2018/127702
PCT Pub. Date: Jul. 12, 2018

(65) Prior Publication Data
US 2019/0350846 A1 Nov. 21, 2019

(30) Foreign Application Priority Data

Jan. 6, 2017 (GB) ...................................... 1700259
Oct. 2, 2017 (GB) ...................................... 1716047

(51) Int. Cl.
*A61K 9/28* (2006.01)
*A61K 9/00* (2006.01)
(Continued)

(52) U.S. Cl.
CPC .............. *A61K 9/0053* (2013.01); *A61K 9/16* (2013.01); *A61K 9/1617* (2013.01); *A61K 9/1623* (2013.01); *A61K 9/2013* (2013.01); *A61K 9/2018* (2013.01); *A61K 9/2095* (2013.01); *A61K 9/28* (2013.01); *A61K 9/4833* (2013.01); *A61K 9/4858* (2013.01); *A61K 9/4891* (2013.01); *A61K 38/28* (2013.01);
(Continued)

(58) Field of Classification Search
CPC ................................ A61K 9/0053; A61K 9/20
See application file for complete search history.

(56) References Cited

U.S. PATENT DOCUMENTS 4,296,130 A 10/1981 Herschler
10,029,007 B2 * 7/2018 Drew ..................... A61K 47/20
(Continued)

FOREIGN PATENT DOCUMENTS

CN 102264760 A 11/2011
CN 103221423 A 7/2013
(Continued)

OTHER PUBLICATIONS

George T. Mercier et al. "Oral immunization of rhesus macaques with adenoviral HIV vaccines using enteric-coated capsules." Vaccine, vol. 25, 2007, pp. 8687-8701. (Year: 2007).*
(Continued)

*Primary Examiner* — Isaac Shomer
(74) *Attorney, Agent, or Firm* — Clark & Elbing LLP; Susan M. Michaud

(57) ABSTRACT

The invention is in the field of delivery of transgenes to target cells using viral vectors, particularly in the field of gene therapy. Compositions have been identified which allow for oral administration of viral particles, particularly adenoviral particles.

12 Claims, 10 Drawing Sheets

(51) Int. Cl.

| | |
|---|---|
| *A61K 9/16* | (2006.01) |
| *A61K 9/20* | (2006.01) |
| *A61K 9/48* | (2006.01) |
| *A61K 38/28* | (2006.01) |
| *A61K 38/46* | (2006.01) |
| *A61K 39/00* | (2006.01) |
| *A61K 39/12* | (2006.01) |
| *A61K 39/245* | (2006.01) |
| *C12N 7/00* | (2006.01) |

(52) U.S. Cl.
CPC ............ *A61K 38/465* (2013.01); *A61K 39/12* (2013.01); *A61K 39/245* (2013.01); *C12N 7/00* (2013.01); *C12Y 301/01008* (2013.01); *A61K 2039/542* (2013.01); *C12N 2710/10343* (2013.01); *C12N 2710/10351* (2013.01); *C12N 2710/10371* (2013.01); *C12N 2710/16034* (2013.01); *C12N 2710/16071* (2013.01); *C12N 2770/24134* (2013.01); *C12N 2770/24171* (2013.01)

(56) References Cited

U.S. PATENT DOCUMENTS

| | | | | |
|---|---|---|---|---|
| 10,086,064 | B2 * | 10/2018 | Drew | A61K 47/26 |
| 10,716,859 | B2 * | 7/2020 | Drew | A61K 47/26 |
| 10,806,783 | B2 * | 10/2020 | Drew | A61K 9/19 |
| 10,980,871 | B2 * | 4/2021 | Drew | A61K 31/198 |
| 2005/0163756 | A1 | 7/2005 | During | |
| 2006/0140908 | A1 | 6/2006 | Ertl | |
| 2008/0120734 | A1 | 5/2008 | Kieffer et al. | |
| 2012/0219590 | A1 * | 8/2012 | Patel | A61P 31/20 |
| | | | | 424/233.1 |
| 2013/0129685 | A1 * | 5/2013 | Drew | A61K 47/26 |
| | | | | 424/93.6 |
| 2013/0164296 | A1 * | 6/2013 | Drew | A61K 41/10 |
| | | | | 424/93.1 |

FOREIGN PATENT DOCUMENTS

| | | |
|---|---|---|
| CN | 107096041 A | 8/2017 |
| CN | 108795984 A | 11/2018 |
| EP | 1634956 B1 | 4/2010 |
| EP | 2552478 B1 | 12/2016 |
| JP | H11-507231 A | 6/1999 |
| JP | 2013-505022 A | 2/2013 |
| JP | 2013-524782 A | 6/2013 |
| WO | WO-96/40954 A1 | 12/1996 |
| WO | WO-9640954 A1 * | 12/1996 ......... A01K 67/0271 |
| WO | WO-00/57921 A2 | 10/2000 |
| WO | WO-02/11540 A1 | 2/2002 |
| WO | WO-02/061104 A2 | 8/2002 |
| WO | WO-02/101012 A2 | 12/2002 |
| WO | WO-03/039593 A1 | 5/2003 |
| WO | WO-2007/000668 A2 | 1/2007 |
| WO | WO-2007/038926 A1 | 4/2007 |
| WO | WO-2010/072900 A1 | 7/2010 |
| WO | WO-2010/146598 A2 | 12/2010 |
| WO | WO-2011/034950 A1 | 3/2011 |
| WO | WO-2011/121306 A1 | 10/2011 |
| WO | WO-2012/038607 A1 | 3/2012 |
| WO | WO-2014/060848 A2 | 4/2014 |

OTHER PUBLICATIONS

Christina A Pacak et al. "Tissue specific promoters improve specificity of AAV9 mediated transgene expression following intravascular gene delivery in neonatal mice." Genetic Vaccines and Therapy 6:13, 2008, pp. 1-5. (Year: 2008).*

Chem 1114: Introduction to Chemistry. "Chapter 7.3 Molarity." https://pressbooks.bccampus.ca/chem1114langaracollege/chapter/3-3-molarity/ accessed Oct. 6, 2023, 18 printed pages. (Year: 2023).*

Hoke Jr et al., "History of the restoration of adenovirus type 4 and type 7 vaccine, live oral (Adenovirus Vaccine) in the context of the Department of Defense acquisition system," Article in Press available 2012, published in final edited form as: Vaccine 31(12):1623-32 (2013) (10 pages).

Armstrong, "Covid-19 vaccine development is less Vaxart, more science," Evaluate Vantage. (Feb. 4, 2021) (1 page).

Chen et al., "Oral vaccination with an adenovirus-vectored vaccine protects against botulism," Vaccine. 31(7):1009-11 (2013).

Chilukuri et al., "Adenovirus-mediated gene transfer of human butyrylcholinesterase results in persistent high-level transgene expression in vivo," Chem Biol Interact. 175(1-3):327-31 (2008).

Gabitzsch et al., "Complete Protection of Nasal and Lung Airways Against SARS-CoV-2 Challenge by Antibody Plus Th1 Dominant N- and S-Specific T-Cell Responses to Subcutaneous Prime and Thermally-Stable Oral Boost Bivalent hAd5 Vaccination in an NHP Study," bioRxiv. preprint version (Dec. 9, 2020) (31 pages).

Gurwith et al., "Safety and immunogenicity of an oral, replicating adenovirus serotype 4 vector vaccine for H5N1 influenza: a randomised, double-blind, placebo-controlled, phase 1 study," Lancet Infect Dis. 13(3):238-50 (2013).

Kim et al., "Preventative Vaccines for Zika Virus Outbreak: Preliminary Evaluation," EBioMedicine. 13:315-320 (2016).

Kuschner et al., "A phase 3, randomized, double-blind, placebo-controlled study of the safety and efficacy of the live, oral adenovirus type 4 and type 7 vaccine, in U.S. military recruits," Vaccine. 31(28):2963-71 (2013).

Lecollinet et al., "Improved gene delivery to intestinal mucosa by adenoviral vectors bearing subgroup B and d fibers," J Virol. 80(6):2747-59 (2006).

Lin et al., "Intramuscular rather than oral administration of replication-defective adenoviral vaccine vector induces specific CD8+ T-cell responses in the gut," available in PMC Mar. 30, 2007, published in final edited form as: Vaccine. 25(12):2187-93 (2007) (13 pages).

Liu et al., "Efficient adenovirus-mediated gene transfer to gastric tissue by oral administration," J Gene Med. 11(12):1087-94 (2009).

Matsumoto et al., "Insulin gene transfer with adenovirus vector via the spleen safely and effectively improves posthepatectomized conditions in diabetic rats," J Surg Res. 110(1):228-34 (2003).

Notice of Reasons for Rejection dated Jun. 28, 2022 for Japanese Patent Application No. 2019-537216, Drew, "Virus," filed Jan. 5, 2018 (English translation) (9 pages).

Office Action dated Nov. 1, 2022 for Chinese Patent Application No. 2018800060901, Applicant: Stabilitech Biopharma Ltd, "Virus," (English translation) (24 pages).

Rhee et al., "TLR4 ligands augment antigen-specific CD8+ T lymphocyte responses elicited by a viral vaccine vector," J Virol. 84(19):10413-9 (2010).

Scallan et al., "An adenovirus-based vaccine with a double-stranded RNA adjuvant protects mice and ferrets against H5N1 avian influenza in oral delivery models," Clin Vaccine Immunol. 20(1):85-94 (2013).

Thulé et al., "Regulated hepatic insulin gene therapy of STZ-diabetic rats," Gene Ther. 7(20):1744-52 (2000).

United States Securities and Exchange Commission, "Form 8-K: Current Report: Pursuant to Section 13 or 15(d) of the Securities Exchange Act of 1934," Registrant: Vaxart, Inc., <https://sec.report/Document/0001437749-21-001804/vxrt20210202_8k.htm>, dated Feb. 3, 2021, retrieved Feb. 17, 2021 (4 pages).

Wang et al., "Adenovirus-based oral vaccine for rabbit hemorrhagic disease," Vet Immunol Immunopathol. 145(1-2):277-82 (2012).

Zhang et al., "Adenovirus Vector Live Vaccine—a New Era of Oral Immunization," Life Sciences. 8(4):43-45 (1996).

Zhong, Hui, PhD Dissertation: "Chitosan increases the efficiency of adenovirus vector mediated gene transduction and improves the effect of oral adenoviral-based vaccines," Pathogen Biology, Chinese Academy of Medical Sciences: Peking Union Medical College, 2009 (101 pages).

Alba et al., "Gutless adenovirus: last-generation adenovirus for gene therapy," Gene Therapy. 12 Suppl 1:S18-27 (2005).

Encina et al., "Insulin is secreted upon glucose stimulation by both gastrointestinal enteroendocrine K-cells and L-cells engineered with the preproinsulin gene," Biol Res. 44(3):301-5 (2011).

(56) References Cited

OTHER PUBLICATIONS

International Search Report and Written Opinion dated Mar. 22, 2018 for PCT International Application No. PCT/GB2018/050021, Drew, "Virus," filed Jan. 5, 2018 (8 pages).

Leader et al., "Protein therapeutics: a summary and pharmacological classification," Nat Rev Drug Discov. 7(1):21-39 (2008).

McConnell et al., "Biology of adenovirus and its use as a vector for gene therapy," Hum Gene Ther. 15(11):1022-33 (2004) (14 pages).

Vorburger et al., "Adenoviral gene therapy," Oncologist. 7(1):46-59 (2002).

Wold et al., "Adenovirus vectors for gene therapy, vaccination and cancer gene therapy," author manuscript; available in PMC Jul. 20, 2015, published in final edited form as Curr Gene Ther. 13(6):421-33 (2013) (26 pages).

Gabitzsch et al., "Complete Protection of Nasal and Lung Airways Against SARS-CoV-2 Challenge by Antibody Plus Th1 Dominant N- and S-Specific T-Cell Responses to Subcutaneous Prime and Thermally-Stable Oral Boost Bivalent hAd5 Vaccination in an NHP Study," bioRxiv preprint version (Mar. 26, 2021) (31 pages).

Stewart et al., "Use of adenovirus as a model system to illustrate a simple method using standard equipment and inexpensive excipients to remove live virus dependence on the cold-chain," Vaccine 32(24):2931-8 (May 2014).

"EUDRAGIT L 30 D-55 Specification and Test Methods," Evonik Industries AG. <https://www.stobec.com/DATA/PRODUIT/1598~v~data_8595.pdf>, dated Jul. 4, 2023. (May 2014) (6 pages).

Chen et al., "Stabilization of recombinant human keratinocyte growth factor by osmolytes and salts," J. Pharm. Sci. 85(4):419-22 (1996).

Communication pursuant to Article 94(3) EPC dated Jul. 7, 2023 for European Patent Application No. 18701209.1, Drew, "Virus," filed Jan. 5, 2018 (11 pages).

Communication pursuant to Rule 114(2) EPC dated Jun. 22, 2023 for European Patent Application No. 18701209.1, Drew, "Virus," filed Jan. 5, 2018 (13 pages).

Lloyd et al., "A comparison of glycine, sarcosine, N,N-dimethylglycine, glycinebetaine and N-modified betaines as liposome cryoprotectants" J. Pharm. Pharmacol. 44(6):507-11 (1992).

* cited by examiner

Viral load testing 7d post Zika challenge

VIRUS

FIELD OF THE INVENTION

This invention relates to oral administration of viral particles, particularly adenoviral particles, carrying a transgene, such as a therapeutic protein for gene therapy. The invention relates in particular to methods of delivering a transgene to target cells by orally administering a product comprising viral particles which carry the transgene. The invention also provides capsules and tablets suitable for oral delivery to the patient, which have been packaged with a pharmaceutical composition comprising the viral particles. The invention further provides a method of preparing the viral particles for oral administration to the patient.

BACKGROUND OF THE INVENTION

Viral vectors are commonly used for gene therapy and also as vaccines to express foreign antigens. Adenoviral vectors have a number of advantages over other types of viral vector. For example, adenoviruses are well studied, can be grown into high titre stable stocks, are capable of effectively transducing both dividing and non-dividing cells and are capable of holding large segments of DNA. A large number of gene therapy trials have now been conducted using adenoviral vectors, many of which relate to the treatment of cancer. Other studies have used adenoviruses to express therapeutic proteins in order to correct genetic defects. Nearly all of these clinical trials have indicated that adenoviral vectors are safe and well-tolerated.

Most adenoviral vectors are modified versions of Ad5 (serotype 5) and vectors may either be replication competent or replication incompetent. Replication incompetent vectors typically have the essential E1A and E1B genes deleted and are replaced by an expression cassette with high promoter activity to drive expression of a foreign transgene. Many replication incompetent vectors also lack the E3 and E4 regions. Another type of replication incompetent adenoviral vector is the "helper dependent" vector which has most of its genome deleted but retains origins of replication as well as ~500 base pairs that are required for packaging into virions. These vectors are constructed and propagated in the presence of a replication competent helper adenovirus, which provides the required early and late proteins. The helper adenovirus typically has loxP sites flanking the packaging signal in the genome. The cell lines used to produce the vectors conditionally express Cre recombinase which excises the loxP flanked packaging signal from the helper adenovirus genome therefore allowing for preferential packaging of the helper dependent adenoviral genome (see for example McConnell and Imperiale (2004) Human Gene Therapy, 1022-1033 and Vorburger and Hunt (2002) The Oncologist, 7, 46-59).

Replication incompetent adenoviral vectors have been administered, for example, intranasally or by intrabronchial catheter when expressing cystic fibrosis transmembrane regulator, via intramyocardial or skeletal muscle injection when expressing vascular endothelial growth factor and by intratumoral injection when expressing cytosine deaminase.

SUMMARY OF THE INVENTION

The present inventors have surprisingly found that adenoviral particles may be administered orally. In particular, the present inventors have shown that adenoviral particles carrying insulin under control of a glucose-dependent insulinotropic polypeptide promoter were able to reduce glucose levels in diabetic rats when orally administered. Not only were the adenoviral particles successfully delivered to the gut, but surprisingly the particles entered into cells and allowed for expression of the therapeutic protein. The therapeutic protein was found to be detectable in the peripheral circulation.

The present invention therefore provides a method of delivering a transgene(s) to target cells in a patient, said method comprising oral administration of a product comprising viral particles which carry the transgene.

The invention also provides a tablet or capsule for oral administration to a patient comprising a pharmaceutical composition which comprises viral particles carrying a transgene.

Furthermore, the invention provides a method of preparing viral particles carrying a transgene for oral administration to a patient, said method comprising:
(a) culturing and purifying viral particles carrying the transgene;
(b) formulating the viral particles in a pharmaceutical composition;
(c) optionally drying the composition; and
(d) packaging the composition into tablets or capsules for oral administration to the patient.

DETAILED DESCRIPTION OF THE INVENTION

Figure 1:
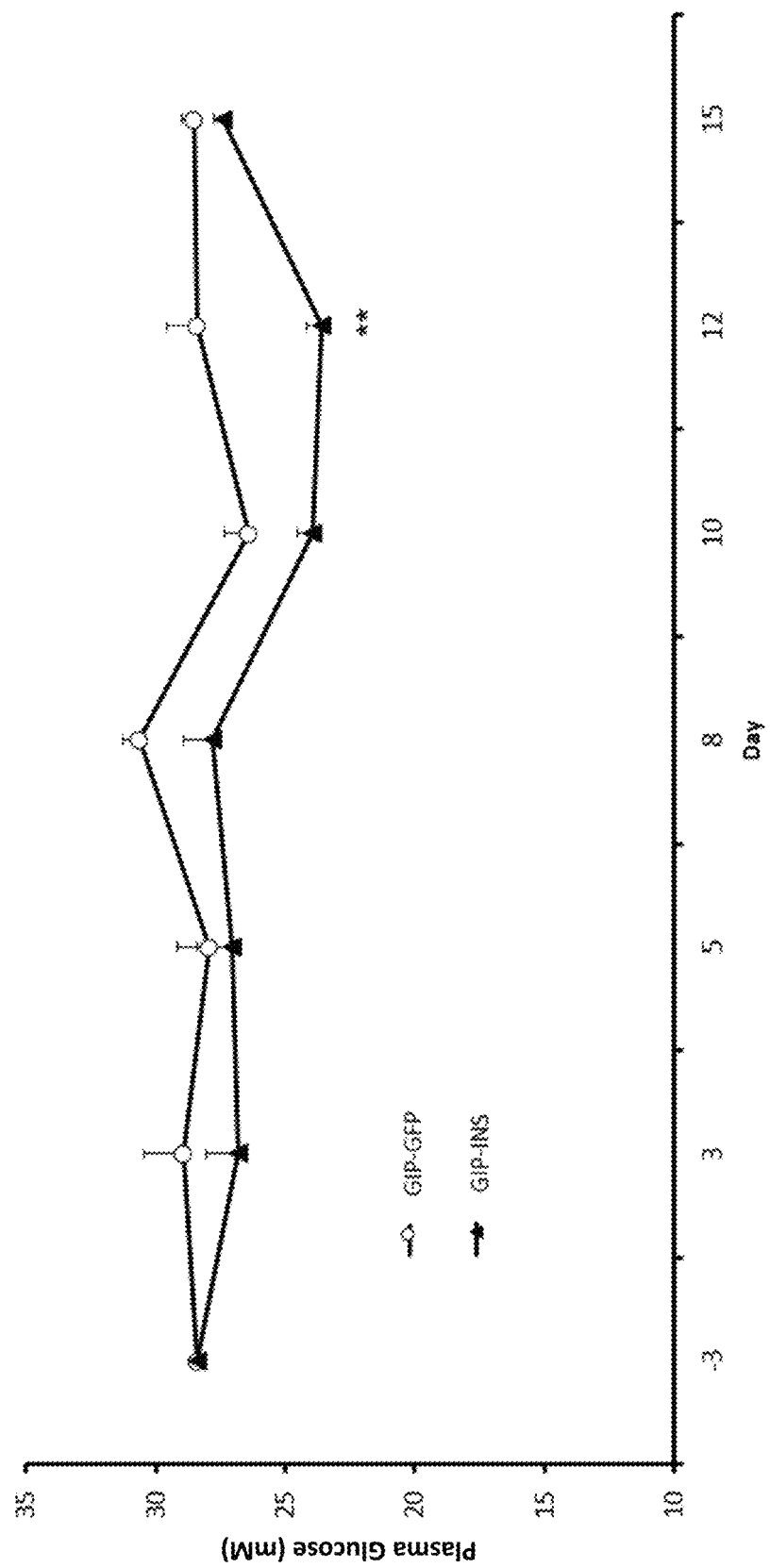
FIG. 1 shows results from the in vivo assessment of oral administration of adenoviral constructs comprising a glucose-dependent insulinotropic polypeptide promoter driving either proinsulin expression or GFP expression. Results presented are for a tail blood vein plasma sample glucose assessment pre (−3 days) or post-dosing (day 3, 5, 8, 10 and 12, with the corresponding dosing at day 1). Data were back-transformed adjusted means (n=5-6). SEMs were calculated from the residuals of the statistical model. Data were analysed by a general linear model with treatment as a factor and Day 1 body weight and log(Day −3) plasma glucose as covariates followed by Dunnett's test. Significant differences vs vehicle are donated with **p<0.01.

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an amino acid sequence" includes two or more such sequences, and the like.

All publications, patents and patent applications cited herein, whether supra or infra, are hereby incorporated by reference in their entirety.

Transgene

The present invention provides a method of delivering a transgene to a patient. In particular, the invention provides a method of delivering a transgene to target cells in a patient. The method comprises oral administration of viral particles, particularly adenoviral particles, which carry the transgene.

A transgene (or heterologous gene), as used herein, is intended to refer to polynucleotide which has been introduced into a cell by genetic manipulation. The transgene could be a gene which is not naturally expressed by the cell. The transgene could also be a gene which would naturally be expressed by a cell. For example, a transgene could supplement natural expression of a protein or could correct deficiencies in expression of a protein.

The transgene typically encodes a therapeutic protein. The methods of the invention are typically gene therapy methods, wherein nucleic acids are therapeutically delivered into a patient's cells followed by expression of the therapeutic protein in order to treat disease. Therapeutic proteins may for example be hormones or enzymes.

Therapies using proteins and peptides may be classified based on function and therapeutic application (see e.g. Leader et al (2008) Nature Reviews Drug Discovery, 7, 21-39). For example, therapeutic proteins may have enzymatic or regulatory activity (Group 1). Therapeutics in group 1 may replace a protein that is abnormal or deficient (often involved in endocrine or metabolic disorders), augment an existing pathway (e.g. haematological and endocrine pathways and immune responses) or provide a novel function or activity. Examples of proteins in this category include albumin, insulin, Factor VIII, Factor IX and anti-thrombin III, enzymes such as pancreatic enzymes, lactase, β-glucocerebrosidase, alglucosidase-alaronidase, idursulphase, galsuphase, adenosine deaminase and other proteins such as erythropoietin, darbepoetin-α, G-CSF, GM-CSF, interleukin 11, follicle stimulating hormone, human chorionic gonadotrophin and various interferons. Examples of therapeutics augmenting an existing pathway include keratinocyte growth factor, platelet derived growth factor and trypsin.

Examples of proteins providing a novel function or activity include botulinum toxin, collagenase, hyaluronidase, papain and streptokinase.

Therapeutic proteins/peptides in group 2 have a specific targeting activity and may interfere with a molecule or organism or deliver other compounds or proteins. For example, proteins in group 2 may bind to molecules and block their function, target them for destruction or stimulate a signalling pathway. Examples include antibody based drugs and Fc fusion proteins.

In the methods of the invention, therapeutic proteins may be in group 1 or group 2. In other words, in the present invention the therapeutic protein may replace a protein that is abnormal or deficient, augment an existing pathway or provide a novel function or activity. The therapeutic protein may also have specific targeting activity, such as an antibody or Fc fusion protein.

Group 3 molecules protect against a deleterious foreign agent, treat an autoimmune disease or treat cancer (protein vaccines). Typically, these comprise an antigenic component from a microorganism, such as Zika virus or Herpes Simplex Virus (HSV) (preferably HSV2), or from a tumour. In the methods of the invention, therapeutic proteins may also be group 3 therapies. In other words, the therapeutic protein may be an antigen.

In some cases, the transgene may also encode a diagnostic agent, such as a fluorescent protein or a protein which may be detected by external scanners.

The viral vector is though preferably a gene therapy vector. The viral vector may also be a vaccine vector which expresses an antigen.

The therapeutic, e.g. when used in gene therapy, is typically a full length protein. The therapeutic may also be a functional variant, modified form or sequence variant which retains one or more activities (preferably all activities) of the full-length counterpart.

In the invention, the therapeutic protein is not particularly limited provided that it would benefit from oral administration of the nucleic acid encoding it to a patient and include hormones and enzymes. Such proteins would be well known from the skilled person's common general knowledge and include, for example, insulin, a glucagon antagonist, glucagon-like peptide-1, resistin, leptin, Acrp30, cholecystokinin, clotting factors (e.g. Factor VIII, IX or X) growth factors, (e.g. growth hormone, insulin-like growth factor 1, platelet derived growth factor, epidermal growth factor, acidic and basic fibroblast growth factors, transforming growth factor β, etc) and antibodies (e.g., human or humanized).

Additional transgenes encoding a therapeutic protein include cytokines, interferons (e.g., interferon (INF), INF-α 2b and 2α, INF-α N1, INF-β 1b, INF-gamma), interleukins (e.g., IL-1 to IL-10), tumor necrosis factor (TNF-α TNF-β), chemokines, granulocyte macrophage colony stimulating factor (GM-CSF), polypeptide hormones, antimicrobial polypeptides (e.g., antibacterial, antifungal, antiviral, and/or antiparasitic polypeptides), enzymes (e.g., adenosine deaminase), gonadotrophins, chemotactins, lipid-binding proteins, filgastim, hemoglobin, erythropoietin, insulinotropin, imiglucerase, sarbramostim, tissue plasminogen activator (tPA), urokinase, streptokinase, neurite growth factor (NGF) phenylalanine ammonia lyase, brain-derived neurite factor (BDNF), neurite growth factor (NGF), phenylalanine ammonia lyase, thrombopoietin (TPO), superoxide dismutase (SOD), adenosine deamidase, catalase calcitonin, endothelian, L-asparaginase pepsin, uricase trypsin, chymotrypsin elastase, carboxypeptidase lactase, sucrase intrinsic factor, calcitonin parathyroid hormone (PTH)-like, hormone, soluble CD4, and antibodies and/or antigen-binding fragments (e.g, FAbs) thereof (e.g., orthoclone OKT-e (anti-CD3), GPIIb/IIa monoclonal antibody).

As mentioned above, the transgenes are not intended to limit the invention. The skilled person could readily envision additional transgenes encoding therapeutic proteins.

The target cells are typically gut cells. The gut is the largest endocrine organ in the body capable of producing vast quantities of proteins and contains rapidly renewing tissue in which the dividing cells are accessible. Target cells, such as K cells and stem cells, are predominantly located in the upper gut which is readily accessible to non-invasive gene therapy techniques like oral formulations. Therefore, gut cells, such as K cells, that secrete a protein, such as insulin, leptin, glucagon antagonist, GLP-1, GLP-2, Ghrelin, cholecystokinin, growth hormone, clotting factors, antibody, among others, in a regulatable fashion is a means with which to treat e.g. diabetes, obesity, growth deficiency and other disorders treatable by producing a protein in mucosal tissue.

In the invention, the therapeutic protein is preferably insulin. Accordingly, the invention provides a method for treating diabetes comprising the oral administration of adenoviral particles encoding insulin to a patient in need thereof. Other secondary disorders or conditions associated with diabetes may also be treated, including kidney tube calcification, degeneration of the liver, eye damage (diabetic retinopathy), diabetic foot, ulcerations, excess bleeding, delayed wound healing, delayed coagulation, increased risk of coronary heart disease, stroke, vascular disease, dyslipidemia, hypertension and obesity.

The methods of the invention may be used to treat and/or prevent a disease or condition (in other words, methods of the invention may be therapeutic or prophylactic). Patients may already have a disease/condition, or may be at risk of developing a disease/condition. Treatment usually results in reducing or preventing the severity or symptoms of the disease/condition in the subject. Treatment may prevent worsening of the disease/condition or reverse the condition/disease. For example, delivery of insulin may reduce blood glucose, improve glucose tolerance, provide normal glucose homeostasis or prevent, improve or reverse a histopathological change such as those mentioned above.

The sequence of the insulin can be any appropriate therapeutic insulin sequence. For example, if the patient is a human, the insulin could be a therapeutic human insulin. The transgene could for example encode a subsequence of full-length insulin that retains ability to lower glucose, provides normal glucose homeostasis or reduces the histopathological conditions associated with chronic or acute hyperglycemia, i.e. a functional subsequence that has one or more activities of its full length counterpart. Such sequences are well known in the art.

Another example of a therapeutic protein suitable for administration using the methods of the present invention is butyrylcholinesterase. Once again, the sequence of butyrylcholinesterase is not limited provided it is appropriate for therapeutic use in the patient (i.e. to treat butyrylcholinesterase deficiency).

The present invention could also be used for the delivery of genetic payloads, such as gene editing payloads (CRISPR).

As mentioned above, in some instances the transgene/therapeutic protein is an antigen (i.e. designed to stimulate an immune response in the host). The viral vector may therefore be a vaccine vector which expresses an antigen and protects the host from challenge with (e.g. the microorganism) from which the antigen is derived. The antigen is not limited, but may typically be derived from a virus. Antigens capable of stimulating an immune response are known in the art.

Figure 9:
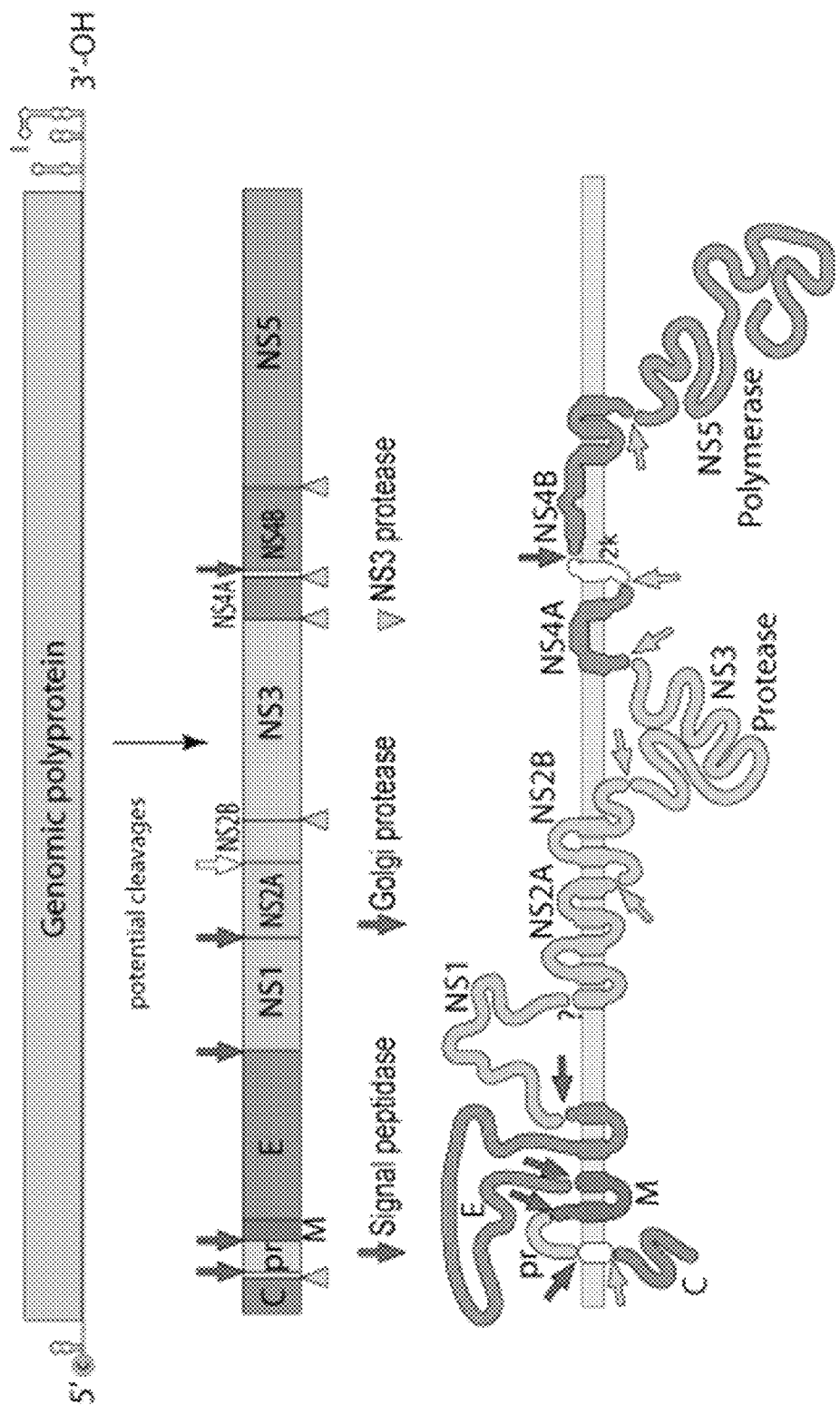
FIG. 9 shows the Zika virus genome.

The antigen may be derived from Zika virus. As shown in FIG. 9, the Zika virus genome encodes various proteins. A vaccine vector of the present invention may express one or more of these proteins. Typically, the vaccine vector expresses the envelope protein E and/or NS1. Envelope protein E is involved in the direct recognition of viral particles and NS1 is believed to play a significant role in disease pathogenesis. The vector may be designed to express either a full-length antigenic sequence, or an antigenic region of the full-length sequence (for example an antigenic region of the E protein, or the complete E protein). Such antigens could readily be determined. A demonstrated in the Examples, expression of such antigens may be under control of a CMV promoter. The skilled person could readily design cassettes for the expression of antigens.

The antigen may also be derived from Herpes Simplex Virus (HSV), preferably from HSV2. The transgene may encode any appropriate HSV antigen capable of stimulating an immune response. Various HSV antigens are known in the art.

For example, glycoprotein D (gD) is expressed on the viral surface and is known to be responsible for neutralising antibody activity. Other HSV glycoproteins include glycoprotein C (gC) and glycoprotein E (gE). The transgene may encode an antigen from any of gD, gC and gE (or combinations thereof). Once again, the transgene may encode (i.e. result in the expression of) the full length protein or an antigenic region of the protein (with any appropriate modifications as determined by the skilled person).

The transgene may in particular encode antigens from all of gD, gC and gE (in some instances, the transgene may encode all of gD, gC and gE). For example, the transgene may express a polyprotein. Expression of such HSV antigens may be under the control of an appropriate promoter and may include other appropriate regulatory sequences. A polyprotein expressed by the transgene may be cleavable (in some instances, the polyprotein may be self-cleavable). The skilled person could readily design appropriate cassettes for the expression of such HSV antigens.

Viral Particles

As discussed further below, the invention is typically performed using adenoviral particles. However, other suitable viruses are adeno-associated viruses, lentiviruses and oncolytic viruses such as HSV and Vaccinia viruses. Viruses with therapeutic applications are well known in the art.

Adenoviral Particles

The methods of the invention typically involve oral administration of adenoviral particles to a patient. Adenoviruses have been widely studied as infectious agents, as a subject for basic research, and for their potential use in gene therapy and vaccines. A large number of human adenoviral serotypes have been identified and they are categorized into six subgenera (A through F) based on nucleic acid comparisons, fibre protein characteristics, and biological properties. For example, group A includes serotypes 12 and 31, group B includes serotypes 3 and 7, group C includes serotypes 2 and 5, group D includes serotypes 8 and 30, group E includes serotype 4, and group F includes serotypes 40 and 41.

In terms of general structure, all adenoviruses examined to date are nonenveloped, regular icosahedrons of about 80 nanometers in diameter. Adenoviruses contain linear, double-stranded DNA that is complexed with core proteins and surrounded by the adenoviral capsid. Individual virions contain about 11 different proteins designated by Roman numerals (II-XII), in order of their decreasing size on SDS gels.

The capsid is composed of seven structural proteins: II (hexon), III (penton), Ma, IV (fiber), VI, VII, and IX. The capsid comprises 252 capsomeres, of which 240 are hexon capsomeres and 12 are penton capsomeres. Hexon capsomeres, which are trimers of the hexon protein, make up about 75% of the protein of the capsid. Penton capsomeres, which are pentamers of the penton protein, are situated at each of the 12 vertices of the virion. Each penton capsomer is bound to six adjacent hexon capsomeres and a fiber. The fiber, which is usually a trimer of the fiber protein, projects from the penton capsomer. The hexon protein and, to a lesser extent, the fiber protein comprise the main antigenic determinants of an adenovirus and also determine serotype specificity.

Researchers have examined and compared the structure of the capsid proteins of different adenoviral serotypes, and in particular hexon proteins, in an effort to define the regions of the proteins against which neutralizing antibodies are elicited. The predominant regions in hexon protein against which neutralizing antibodies are directed appear to be in loops 1 and 2 (i.e., LI or l1, and LII or l2, respectively), which project outward from the base of the hexon capsomere. Analysis of loops 1 and 2 from different adenovirus hexon proteins has revealed the presence of seven discrete hypervariable regions (HVR1 to HVR7) corresponding to locations where the hexon proteins differ considerably between serotypes.

The core of an adenovirus virion contains the linear double-stranded DNA genome and associated proteins V, VII, X (mu), IVa2, and terminal protein (TP). The genome organization of different adenoviruses is conserved and has been proposed to have a timing function, wherein the ends of the genome are transcribed first (the immediate early genes E1 and E4 are located at opposite ends of the linear genome). Early transcription of E1 and E4 leads to the opening of the central region of the genome, allowing transcription of the central region.

Adenoviral genomes typically comprise eight RNA polymerase II transcriptional units: five early units, E1A, E1B, E2A-E2B, E3, and E4; two delayed early units, IX and IVa2; and the Major Late transcriptional unit. The Major Late transcriptional unit is further subdivided into L1-L5 regions based upon the use of alternative splicing sites. The transcriptional units often express proteins of similar function. For example, the E1A unit codes for two proteins responsible for activation of transcription and induction of S-phase upon cellular infection; the E1B transcription unit encodes two proteins that inhibit cellular apoptosis; the E3 transcriptional unit is involved in evasion of the immune response; and the Major Late transcriptional unit encodes structural proteins necessary for assembly of the capsid.

For the purpose of gene therapy and vaccination, recombinant adenoviral vectors have been designed to encode and express heterologous genes and antigens. The Ad2 and Ad5 serotypes have been used most extensively in this context. Heterologous sequences have been inserted into the adenoviral genomes, including in the early transcriptional units and in the coding regions of various structural proteins, such as hexon, penton, and fiber. In many cases, deletions in the adenoviral genome (e.g., in the E1 regions) have been used to create replication-defective adenoviral vectors, which have generally been considered safer for administration to human subjects.

In the present invention, the adenovirus may be any adenovirus suitable for delivery of the transgene to target cells. For example, the adenovirus may be any serotype but is typically Ad5. The term "adenoviral vector" refers to a wild-type, mutant, and/or recombinant adenoviral genome, as well as adenoviruses comprising such a genome. An adenoviral vector can comprise all or part of the genome of any adenoviral serotype, as well as combinations thereof (i.e., hybrid genomes).

The adenoviral vector used in the invention may be either replication competent or replication competent. Such vectors are well known. For example, in a replication incompetent vector the E1 region may be deleted and replaced with an expression cassette with an exogenous promoter driving expression of the heterologous transgene. Usually, the E3 region is also deleted. Deletion of E3 allows for larger inserts into the E1 region. Such vectors may be propagated in appropriate cell lines such as HEK 293 cells which retain and express the E1A and E1B proteins. Later generation vectors also lack the E4 region, and some vectors further lack the E2 region. E2 and E4 vectors must be grown on cell lines that complement the E1, E4 and E2 deletions.

Vectors may also be helper dependent vectors, which lack most or all of the adenoviral genes but retain cis-acting sequences such as the inverted terminal repeats as well as packaging sequences that are required for the genome to be packaged and replicated. These vectors are propagated in the presence of a helper adenovirus, which must be eliminated from the vector stocks. Once again, such systems are well known in the art.

In the invention, the vector is typically a replication incompetent vector (such as an E1/E3 deletion vector as used in the Examples), but the vector could also be helper-dependent or replication competent. Replication competent vectors are well known. The skilled person would readily be able to select an appropriate vector system depending on the intended application.

Expression of the transgene can be driven via operable linkage to an appropriate promoter. Vectors used in the present invention may use other appropriate expression control elements, such as enhancers and regulators. Enhancers are broadly defined as a cis-acting agent, which when operably linked to a promoter/gene sequence, will increase transcription of that gene sequence. Enhancers can function from positions that are much further away from a sequence of interest than other expression control elements (e.g. promoters) and may operate when positioned in either orientation relative to the sequence of interest. Enhancers have been identified from a number of viral sources, including adenoviruses.

Adenoviral vectors may use high activity promoters such as the cytomegalovirus (CMV) promoter, SV40 large T antigen promoter, mouse mammary tumour virus LTR promoter, adenovirus major late promoter (MLP), the mouse mammary tumour virus LTR promoter or the SV40 early promoter.

The vectors may also use an appropriate promoter to switch on expression of the transgene when necessary e.g. in target cells (tissue specific promoters or inducible promoters). Promoters may be selected to be compatible with the target cell for which expression is designed.

Tissue specific promoters are typically active in a particular cell type because they are recognised by transcriptional activator proteins, or other regulators of transcription, which are specific to that cell type. For example, in the invention the promoter may be capable of targeting expression of the transgene to endocrine cells in the gut (a "gut endocrine cell specific promoter").

The promoter may maintain the transcriptional homeostasis of the transgene product in response to stimuli generated from the activity of the transgene product.

Expression of the transgene is preferably controlled via operable linkage to the glucose-dependent insulinotropic polypeptide promoter (GIP), which is a specific example of a gut endocrine cell promoter. When this construct is introduced into endocrine cells, the encoded protein will be expressed and secreted in a regulated manner. The GIP promoter has previously been shown to target expression and secretion of human insulin in K cells of the gastrointestinal tract. Most preferably, the GIP promoter is used to control expression of insulin.

The Examples of the present application use a 1.2 kb rat GIP insert as described in Biol. Res. (2011) 44, 301-305. The skilled person would though readily be able to select an appropriate promoter depending on the application.

Other examples of tissue specific promoters and enhancers for targeting expression of proteins to endocrine cells in the gut are glucokinase, chromogranin A and B, cholecystokinin, proglucagon, adenosine deaminase, secretin, gastrin, somatostatin, motilin and ghrelin. Tissue-specific expression control elements may be active in other tissues but to a much lesser extent than in the target tissue. Promoters may also increase or decrease expression of an operably linked nucleic acid in response to or withdrawal of a nutrient. Such nutrient-regulatable elements are also widely known. Other expression control elements may be constitutively active, or may confer expression at a particular stage of the cell cycle.

As used herein, the term "operable linkage" or grammatical variations thereof refers to a physical or functional juxtaposition of the components so described as to permit them to function in their intended manner. In the example of an expression control element in operable linkage with a nucleic acid, the relationship is such that the control element modulates expression of the nucleic acid.

Formulations Comprising the Viral Particles

The viral particles are formulated with excipients which provide thermal stability.

WO 2011/121306 discloses formulations which were capable of stabilising viral particles against damage caused by freezing, freeze drying and thawing. Virus activity was also preserved during long-term stability tests.

In the present invention, the viral particles may be formulated in a composition which comprises a compound of formula (I) or a physiologically acceptable salt or ester thereof and/or a compound of formula (II) or a physiologically acceptable salt or ester thereof and optionally one, two or more sugars. The viral particles are typically contacted with the compound of formula (I) or a physiologically acceptable salt or ester thereof and/or compound of formula (II) or a physiologically acceptable salt or ester thereof and optionally one or more sugars in an aqueous solution and the resulting solution in which the viral particles are present is then dried to form a composition incorporating the viral particles.

The viral particles may therefore be admixed with an aqueous solution of the compound of formula (I) or a physiologically acceptable salt or ester thereof and/or compound of formula (II) or a physiologically acceptable salt or ester thereof and optionally one or more sugars. The resulting solution is then dried to form a composition incorporating the viral particles. The dried composition may take the form of a cake or powder. The cake can be milled to a powder if required.

The viral particles are preserved in the aqueous solution prior to the drying step. This allows the aqueous solution to be stored after preparation, until such time as the drying step can be carried out, without undue loss of viral activity The compounds of formula (I) and (II) may be present as a physiologically acceptable salt or ester thereof.

The salt is typically a salt with a physiologically acceptable acid and thus includes those formed with an inorganic acid such as hydrochloric or sulphuric acid or an organic acid such as citric, tartaric, malic, maleic, mandelic, fumaric or methanesulphonic acid. The hydrochloride salt is preferred.

The ester is typically a $C_{1-6}$ alkyl ester, preferably a $C_{1-4}$ alkyl ester. The ester may therefore be the methyl, ethyl, propyl, isopropyl, butyl, isobutyl or tert-butyl ester. The ethyl ester is preferred.

As used herein, a $C_{1-6}$ alkyl group is preferably a $C_{1-4}$ alkyl group. Preferred alkyl groups are selected from methyl, ethyl, propyl, isopropyl, butyl, isobutyl and tert-butyl. Methyl and ethyl are particularly preferred.

For the avoidance of doubt, the definitions of compounds of formula (I) and formula (II) also include compounds in which the carboxylate anion is protonated to give —COOH and the ammonium or sulfonium cation is associated with a pharmaceutically acceptable anion. Further, for the avoidance of doubt, the compounds defined above may be used in any tautomeric or enantiomeric form.

Compounds of Formula (I)

Typically, $R_1$ represents hydrogen or $C_{1-6}$ alkyl and $R_4$ represents hydrogen. Typically, $R_2$ represents hydrogen or $C_{1-6}$ alkyl. Preferably, $R_1$ represents hydrogen or $C_{1-6}$ alkyl, $R_4$ represents hydrogen and $R_2$ represents hydrogen or $C_{1-6}$ alkyl. More preferably $R_1$ represents hydrogen or $C_{1-6}$ alkyl, $R_4$ represents hydrogen and $R_2$ represents $C_{1-6}$ alkyl.

Preferably, the compound of formula (I) is an N—$C_{1-6}$ alkyl-, N,N-di($C_{1-6}$ alkyl)- or N,N,N-tri($C_{1-6}$ alkyl)-glycine or physiologically acceptable salt or ester thereof, more preferably an N,N-di($C_{1-6}$ alkyl)- or N,N,N-tri($C_{1-6}$ alkyl)-glycine or physiologically acceptable salt or ester thereof. The alkyl group is typically a $C_{1-4}$ alkyl group. Preferred alkyl groups are selected from methyl, ethyl, propyl, isopropyl, butyl, isobutyl and tert-butyl. Methyl and ethyl are particularly preferred.

Preferred compounds of formula (I) are N-methylglycine, N,N-dimethylglycine or N,N,N-trimethylglycine or physiologically acceptable salts or esters thereof. N-Methylglycine is also called sarcosine. N,N-Dimethylglycine is also termed dimethylglycine (DMG) or 2-(dimethylamino)-acetic acid. N,N,N-trimethylglycine is termed trimethylglycine (TMG). The most preferred compound of formula (I) is DMG.

Alternatively, the compound of formula (I) is typically a glycine derivative of formula (IA) or a physiologically acceptable salt or ester thereof:

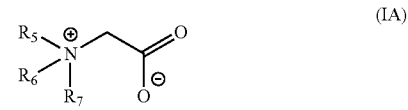

(IA)

wherein $R_5$ and $R_6$ independently represent $C_{1-6}$ alkyl, for example $C_{1-4}$ alkyl such as methyl or ethyl; and $R_7$ represents $C_{1-6}$ alkyl, for example $C_{1-4}$ alkyl such as methyl or ethyl, or —$(CH_2)_{2-5}$NHC(O)$(CH_2)_{5-15}CH_3$. Preferred compounds of formula (IA) are trimethylglycine (TMG) and cocamidopropyl betaine (CAPB) or physiologically acceptable salts or esters thereof. Trimethyglycine is preferred.

Alternatively, the compound of formula (I) is typically a proline derivative of formula (IB) or a physiologically acceptable salt or ester thereof:

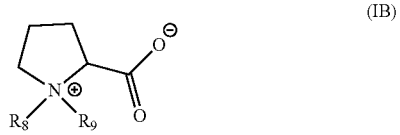
(IB)

wherein $R_8$ and $R_9$ independently represent $C_{1-6}$ alkyl, for example $C_{1-4}$ alkyl such as methyl or ethyl. Preferably the compound of formula (IB) is an S-proline derivative. Preferably $R_8$ and $R_9$ both represent methyl; this compound is known as proline betaine. S-proline betaine or physiologically acceptable salt or ester thereof is particularly preferred:

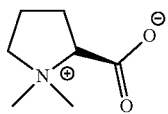

Compounds of formula (IA) or physiologically acceptable salts or esters thereof are preferred.

Preferably, the compound of formula (I) is N, N-dimethylglycine or N, N, N-trimethylglycine or physiologically acceptable salt or ester thereof. Most preferably, the compound of formula (I) is N, N-dimethylglycine or physiologically acceptable salt or ester thereof.

Compounds of Formula (II)

Typically, the carboxylate and amine substituents of $R_c$ are attached to the same carbon atom of the $R_c$ alkyl moiety. Typically $R_c$ is a $C_{2-4}$ or $C_{2-3}$ alkyl moiety.

The compound of formula (II) is typically a sulfone compound of formula (IIA) or a physiologically acceptable salt or ester thereof:

(IIA)

wherein $R_c$ and $R_d$ independently represent $C_{1-6}$ alkyl, for example $C_{1-4}$ alkyl. Preferred alkyl groups are selected from methyl, ethyl, propyl, isopropyl, butyl, isobutyl and tert-butyl. Methyl and ethyl are particularly preferred. The most preferred sulfone compound is methylsulfonylmethane (MSM), which is also known as dimethylsulfone ($DMSO_2$).

The compound of formula (II) may be a compound of formula (IIB) or a physiologically acceptable salt or ester thereof:

(IIB)

wherein $R_e$ and $R_f$ independently represent $C_{1-6}$ alkyl, for example $C_{1-4}$ alkyl such as methyl or ethyl, and $R_g$ represents $C_{1-6}$ alkyl, for example $C_{1-4}$ alkyl such as methyl or ethyl, substituted with a carboxylate anion and with an amine (—$NH_2$) moiety. Preferably the carboxylate and amine substituents are attached to the same carbon atom. A preferred compound of formula (IIB) is S-methyl-L-methionine (SMM) or a physiologically acceptable salt or ester thereof.

In the present invention, it is most preferred that the compound of formula (I) is DMG or a physiologically acceptable salt or ester thereof and the compound of formula (II) is MSM or a physiologically acceptable salt or ester thereof Sugars Sugars suitable for use in the present invention include reducing sugars such as glucose, fructose, glyceraldehydes, lactose, arabinose and maltose; and preferably non-reducing sugars such as sucrose and raffinose, more preferably sucrose. The sugar may be a monosaccharide, disaccharide, trisaccharide, or other oligosaccharides. The term "sugar" includes sugar alcohols. In one embodiment, therefore, use of a non-reducing sugar or a sugar alcohol is preferred.

Monosaccharides such as galactose and mannose; dissaccharides such as sucrose, lactose and maltose; trisaccharides such as raffinose; and tetrasaccharides such as stachyose are envisaged. Trehalose, umbelliferose, verbascose, isomaltose, cellobiose, maltulose, turanose, melezitose and melibiose are also suitable for use in the present invention. A suitable sugar alcohol is mannitol. When mannitol is used, cakes of improved appearance can be obtained on freeze-drying.

The presence of sugar may act to improve stability. The addition of sugar may also provide other benefits such as an altered lyophilisation cake and improved solubility for faster reconstitution. Generally one or more sugars is present when freeze-drying is used. When one sugar is used, the sugar is preferably sucrose or mannitol.

Preservation of viral activity is particularly effective when two or more sugars are used in the preservation mixture. Two, three or four sugars may be used. Preferably, the aqueous solution is a solution of sucrose and raffinose. Sucrose is a disaccharide of glucose and fructose. Raffinose is a trisaccharide composed of galactose, fructose and glucose.

In the present invention, the compound of formula (I) is preferably DMG or a physiologically acceptable salt or ester thereof and the compound of formula (II) is preferably MSM or a physiologically acceptable salt or ester thereof. The composition preferably also comprises sucrose.

Other Components of the Aqueous Composition

In the present invention, an aqueous solution comprising the viral particles, optionally one or more sugars and a compound of formula (I) or a physiologically acceptable salt or ester thereof and/or a compound of formula (II) or a physiologically acceptable salt or ester thereof is typically dried. Any suitable aqueous solution may be used. The solution may be buffered. The solution may be a HEPES, phosphate-buffered, Tris-buffered or pure water solution.

The solution may have a pH of from 2 to about 12 and may be buffered. The solution may be buffered with HEPES buffer, phosphate-buffer, Tris-buffer, sodium citrate buffer, bicine buffer (i.e. N,N-bis(2-hydroxyethyl) glycine buffer) or MOPS buffer (i.e. 3-(N-morpholino) propanesulfonic acid buffer). The solution may or may not contain NaCl. The solution may thus be a saline sodium citrate (SSC) buffered solution.

Generally a preparation of the viral particles is admixed with the preservation mixture, i.e. with an aqueous solution of a compound of formula (I) or a physiologically acceptable salt or ester thereof and/or a compound of formula (II) or a physiologically acceptable salt or ester thereof and optionally one, two or more sugars. The preservation mixture may itself be buffered. It may be a HEPES, phosphate-buffered, Tris-buffered or pure water solution.

Alternatively, the aqueous solution may typically consist, or consist essentially, of viral particles, a compound of formula (I) or a physiologically acceptable salt or ester thereof and/or a compound of formula (II) or a physiologically acceptable salt or ester thereof, and optionally one or more sugars.

The concentrations of the compound of formula (I) or a physiologically acceptable salt or ester thereof and/or a compound of formula (II) or a physiologically acceptable salt or ester thereof and of each optional sugar can be determined by routine experimentation. Optimised concentrations which result in the best stability can thus be selected. The compound of formula (I) or a physiologically acceptable salt or ester thereof and/or a compound of formula (II) or a physiologically acceptable salt or ester thereof compound may act synergistically to improve stability.

The concentration of sugar when present in the aqueous solution for drying is at least 0.01M, typically up to saturation. Generally the sugar concentration when present is at least 0.1M, at least 0.2M or at least 0.5M up to saturation e.g. saturation at room temperature or up to 3M, 2.5M or 2M. The sugar concentration may therefore range from, for example, 0.1M to 3M or 0.2M to 2M. Preferably a sugar is present. Alternatively, the sugar concentration or the total sugar concentration if more than one sugar is present may therefore range from 0.08M to 3M, from 0.15M to 2M or from 0.2M to 1M. A suitable range is from 0.05 to 1M.

When more than one sugar is present, preferably one of those sugars is sucrose. The sucrose may be present at a concentration of from 0.05M, 0.1M, 0.25M or 0.5M up to saturation e.g. saturation at room temperature or up to 3M, 2.5M or 2M.

The ratio of the molar concentration of sucrose relative to the molar concentration of the other sugar(s) is typically from 1:1 to 20:1 such as from 5:1 to 15:1. In the case when two sugars are present and in particular when sucrose and raffinose are present, therefore, the ratio of molar concentrations of sucrose is typically from 1:1 to 20:1 such as from 5:1 to 15:1 and preferably about 10:1.

The concentration of each compound of formula (I) or physiologically acceptable salt or ester thereof or compound of formula (II) or physiologically acceptable salt or ester thereof in the aqueous solution for drying is generally in the range of from 0.001M to 2.5M and more especially from 0.01M to 2.5M. For example, the concentration range may be from 0.1M to 2.5M.

Alternatively, for example when the compound of formula (I) is DMG or a salt or ester, the concentration of each compound of formula (I) or physiologically acceptable salt or ester thereof or compound of formula (II) or physiologically acceptable salt or ester thereof in the aqueous solution for drying is generally in the range of 0.1 mM to 3M or from 1 mM to 2M. The concentration may be from 1 mM to 1.5M or from 5 mM to 1M or from 0.07M to 0.7M. Preferred concentrations are from 7 mM to 1.5M or from 0.07M to 1.2M. Another further preferred range is 0.5 to 1.5M, particularly when the compound of formula (I) is an N-alkylated glycine derivative such as DMG.

The particular concentration of compound of formula (I) or physiologically acceptable salt or ester thereof or compound of formula (II) or physiologically acceptable salt or ester thereof that is employed will depend on several factors including the type of viral particle to be preserved; the particular compound being used; whether one, two more sugars are present and the identity of the sugar(s); and the drying procedure and conditions. Thus:

The concentration of a compound of formula (II) in which X represents —S(O)$_2$— or a compound of formula (IIA), such as MSM, or a physiologically acceptable salt or ester thereof is preferably from 0.2 mM to 1M such as from 0.35 mM to 1M, from 3.5 mM to 0.5M, from 0.035M to 0.5M or from 0.035M to 0.25M.

The concentration of a compound of formula (I) or a compound of formula (IA) or formula (TB), such as TMG, or a physiologically acceptable salt or ester thereof is preferably used at a concentration from 0.01M to 2M such as from 0.07M to 2M, from 0.2M to 1.5M, from 0.23M to 1.5M or from 0.07M to 0.7M.

The concentration of a compound of formula (II) in which X represents —S$^+$(R$_c$)— or a compound of formula (IIB), such as S-methyl-L-methionine, or a physiologically acceptable salt or ester thereof is preferably from 0.005M to 2M such as from 0.007M to 2M, from 0.02M to 2M, from 0.023M to 1.5M or from 0.07M to 1M.

The concentration of a compound of formula (I), such as N,N-dimethylglycine (DMG) or a physiologically acceptable salt or ester thereof, when no sugar is present are from 5 mM to 1.5M or from 70 mM to 1.5M or to 1.2M or from 7 mM to 1M. More preferred concentrations are from 0.023M to 0.7M or 1M, or from 0.07M to 0.7M or 1M, such as about 0.7M The concentration of a compound of formula (I), such as N,N-dimethylglycine (DMG) or a physiologically acceptable salt or ester thereof, when one or more sugars are present are generally lower and in the range of from 1 mM to 1M or 1.5M or from 5 mM to 1M. More preferred concentrations are from 0.007M to 0.7M or 1M such as about 0.007M. A particularly preferred range is 0.5 to 1.5M.

When a compound of formula (I) or physiologically acceptable salt or ester thereof and a compound of formula (II) or physiologically acceptable salt or ester thereof are present, and preferably when an N-alkylated glycine derivative or salt or ester thereof and a sulfone compound of formula (IIA) or (IIC) are present, the compounds can be present in amounts that result in synergy. For example:

The concentration of the N-alkylated glycine derivative or salt or ester thereof in the aqueous solution for drying is generally in the range of 0.1 mM to 3M or from 1 mM to 2M. The concentration may be from 1 mM to 1.5M or from 5 mM to 1M. Preferred concentrations are from 0.1M to 1.5M or from 0.5M to 1.25M.

The concentration of the sulfone compound of formula (IIA) or (IIC) in the aqueous solution for drying is generally in the range of 0.1 mM to 3M, from 1 mM to 2M or from 0.2 mM to 1M. The concentration may be from 0.1M to 1.5M or from 0.5M to 1.25M.

The composition may also comprise other preservatives such as antioxidants, lubricants and binders well known in the art.

Tablets and Capsules

The pharmaceutical compositions described herein may be administered in the form of an aqueous suspension or solution or troche, but are typically administered as a tablet or capsule. The compositions may also be administered as gelatin wafers. Tablets may be coated or un-coated. Preferably, the composition is incorporated into a capsule, such as a gelatine capsule.

Pharmaceutically compatible binding agents, and/or adjuvant materials can be included in oral formulations. The tablets, capsules, troches and the like can contain any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or flavouring.

Capsules and tablets are typically enterically coated. The skilled person would readily be able to select and apply an appropriate enteric coating depending on the transgene to be delivered using methods known in the art. For example, the enteric coating may target delivery to the duodenum. An example of such a coating is poly(methacyclic acid-co-thyl acrylate) 1:1 copolymer as used in the Example. The enteric coating may have a threshold of pH 5.8-6.8.

Delivery of the Viral Particles to a Patient

The patient is typically a human, but could also be an animal such as a domestic, companion (such as a dog or cat) or livestock animal (sheep, pigs, cows).

Administration of the viral particles may be for either prophylactic or therapeutic purposes. The doses or "effective amount" for treating a subject are preferably sufficient to ameliorate one, several or all of the symptoms of the condition, to a measurable or detectable extent, although preventing or inhibiting a progression or worsening of the disorder or condition, or a symptom, is a satisfactory outcome. Doses and frequency of dosing will depend on the condition to be treated and the desired outcome and can be readily ascertained by the skilled person. Appropriate amounts will depend upon the therapeutic effect desired, as well as the individual subject (e.g., the bioavailability within the subject, gender, age, etc.). For example, a partial restoration of normal glucose homeostasis in a subject can reduce the frequency for insulin injection, even though complete freedom from insulin injection has not resulted.

Effective amounts can be ascertained by measuring relevant physiological effects. For example, in the case of diabetes or other hyperglycemic condition, a decrease in blood glucose or an improvement in glucose tolerance test can be used to determine whether the amount of insulin is effective to treat the hyperglycemic condition. In the case of haemophilia, an effective amount is an amount which reduces clotting time or frequency or duration of bleeding episodes in a subject.

The methods of the invention for treating a subject also can be supplemented with other forms of therapy. Supplementary therapies include drug treatment, a change in diet (low sugar, fats, etc.) surgical resection, transplantation, radiotherapy, etc. For example, a method of the invention for treating a hyperglycemic condition can be used in combination with drugs or other pharmaceutical formulations that increase insulin or lower glucose in a subject. Drugs for treating diabetes include, for example, biguanides and sulphonylureas (e.g., tolbutamide, chlorpropamide, acetohexamide, tolazamide, glibenclamide and glipizide). Appetite suppression drugs are also well known and can be used in combination with the methods of the invention. Supplementary therapies can be administered prior to, contemporaneously with or following the invention methods of treatment.

The skilled person could readily ascertain therapies that may be used in a regimen in combination with the treatment methods of the invention.

The invention also provides methods of preventing and/or treating Zika virus infection using the viral particles of the invention. In particular, the viral particles may be used as vaccine for preventing and/or treating Zika virus infection. As discussed above, here the viral vector may express Zika virus antigens, preferably derived from envelope protein E and/or NS1.

Dosages and dosage regimes of a Zika virus vaccine could readily be determined by a person skilled in the art. For example, a prophylatic vaccine may be administered multiple times (for example twice or three times) at appropriate intervals. Such intervals may be once a week, or once a fortnight. For example, a prophylactic vaccine could be administered two or three times approximately once a fortnight (at approximately 14 day intervals).

Method of Preparing Viral Particles

The invention also provides a method of preparing the viral particles for oral administration to a patient. The method typically comprises culturing and purifying the viral particles, formulating the particles into a composition, optionally drying the composition, and packaging the composition into tablets of capsules for oral administration to the patient.

Viral particles carrying a transgene can be prepared using standard techniques well known to those skilled in the art. For example, standard molecular biology techniques can be used to create the genetic constructs for expression of the transgene.

A virus may be prepared by infecting cultured host cells with the virus strain that is to be used, allowing infection to progress such that the virus replicates in the cultured cells and can be released by standard methods known in the art for harvesting and purifying viruses. Suitable cells include Human Embryonic Kidney (HEK) 293 cells, or HEK 293 derived cell clones, which are appropriate for the type of adenovirus being used. The cells may be cultured under any appropriate conditions that result in the production of virus particles.

For example, the Example of the present application uses culture of virus in HEK 293 cells and subsequent purification by double caesium chloride density gradient centrifugation followed by column desalting (e.g. PD-10) into the excipient formulation. Excipient formulations are described above.

Typically, drying is achieved by freeze drying, vacuum drying, fluid bed drying or spray-drying. Freeze-drying is preferred. By reducing the water in the material and sealing the material in a vial, the material can be easily stored, shipped and later reconstituted to its original form. The drying conditions can be suitably optimized via routine experimentation.

On drying, a composition is formed which incorporates the viral particles. A matrix incorporating the viral particles is produced. The composition is typically an amorphous solid. A solid matrix, generally an amorphous solid matrix, is thus generally formed. By "amorphous" is meant non-structured and having no observable regular or repeated organization of molecules (i.e. non-crystalline).

The sugar or sugars when present provide the amorphous matrix in the dried composition. The compound of formula (I) or a physiologically acceptable salt or ester thereof and/or a compound of formula (II) or physiologically acceptable salt or ester thereof is dispersed in the sugar matrix. The compound of formula (I) or a physiologically acceptable salt or ester thereof and/or compound of formula (II) or physiologically acceptable salt or ester thereof is thus incorporated within the sugar matrix. The viral particles are incorporated within the sugar matrix too. The drying procedure can thus be effected e.g. by freeze-drying to form an amorphous cake within which the viral particles are incorporated.

The drying step is generally performed as soon as the aqueous solution has been prepared or shortly afterwards. Alternatively, the aqueous solution is typically stored prior to the drying step. The viral particle in the aqueous solution is preserved by the compound of formula (I) or a physiologically acceptable salt or ester thereof and/or a compound of formula (II) or physiologically acceptable salt or ester thereof and, optionally, one or more sugars during storage.

The aqueous solution, or bulk intermediate solution, is generally stored for up to 5 years, for example up to 4 years, 3 years, 2 years or 1 year. Preferably the solution is stored for up to 6 months, more preferably up to 3 months or up to 2 months, for example 1 day to 1 month or 1 day to 1 week. Prior to drying, the solution is typically stored in a refrigerator or in a freezer. The temperature of a refrigerator is typically 2 to 8° C., preferably 4 to 6° C., or for example about 4° C. The temperature of a freezer is typically −10 to −80° C., preferably −10 to −30° C., for example about −20° C.

The solution is typically stored in a sealed container, preferably a sealed inert plastic container, such as a bag or a bottle. The container is typically sterile. The volume of the bulk intermediate solution is typically 0.1 to 100 litres, preferably 0.5 to 100 litres, for example 0.5 to 50 litres, 1 to 20 litres or 5 to 10 litres. The container typically has a volume of 0.1 to 100 litres, preferably 0.5 to 100 litres, for example 0.5 to 50 litres, 1 to 20 litres or 5 to 10 litres.

If the stored bulk intermediate solution is to be freeze-dried, it is typically poured into a freeze-drying tray prior to the drying step.

There are three main stages to freeze-drying namely freezing, primary drying and secondary drying. Freezing is typically performed using a freeze-drying machine. In this step, it is important to cool the biological material below its eutectic point, (Teu) in the case of simple crystalline products or glass transition temperature (Tg') in the case of amorphous products, i.e. below the lowest temperature at which the solid and liquid phase of the material can coexist. This ensures that sublimation rather than melting will occur in the following primary drying stage.

During primary drying the pressure is controlled by the application of appropriate levels of vacuum whilst enough heat is supplied to enable the water to sublimate. At least 50%, typically 60 to 70%, of the water in the material is sublimated at this stage. Primary drying may be slow as too much heat could degrade or alter the structure of the biological material. A cold condenser chamber and/or condenser plates provide surfaces on which the water vapour is trapped by resolidification.

In the secondary drying process, water of hydration is removed by the further application of heat. Typically, the pressure is also lowered to encourage further drying. After completion of the freeze-drying process, the vacuum can either be broken with an inert gas such as nitrogen prior to sealing or the material can be sealed under vacuum.

In certain embodiments, vacuum drying is carried out using vacuum desiccation at around 1300 Pa. However vacuum desiccation is not essential to the invention and in other embodiments, the preservation mixture contacted with the viral particle is spun (i.e. rotary desiccation) or freeze-dried. Advantageously, the method of the invention further comprises subjecting the preservation mixture containing the viral particle to a vacuum. Conveniently, the vacuum is applied at a pressure of 20,000 Pa or less, preferably 10,000 Pa or less. Advantageously, the vacuum is applied for a period of at least 10 hours, preferably 16 hours or more. As known to those skilled in the art, the period of vacuum application will depend on the size of the sample, the machinery used and other parameters.

In another embodiment, drying is achieved by spray-drying or spray freeze-drying the viral particles admixed with the preservation mixture of the invention. These techniques are well known to those skilled in the art and involve a method of drying a liquid feed through a gas e.g. air, oxygen-free gas or nitrogen or, in the case of spray freeze-drying, liquid nitrogen. The liquid feed is atomized into a spray of droplets. The droplets are then dried by contact with the gas in a drying chamber or with the liquid nitrogen.

In a further embodiment, drying is achieved by fluid bed drying the viral particles admixed with the preservation mixture. This technique is well known to those skilled in the art and typically involves passing a gas (e.g. air) through a product layer under controlled velocity conditions to create a fluidized state. The technique can involve the stages of drying, cooling, agglomeration, granulation and coating of particulate product materials. Heat may be supplied by the fluidization gas and/or by other heating surfaces (e.g. panels or tubes) immersed in the fluidized layer. Cooling can be achieved using a cold gas and/or cooling surfaces immersed in the fluidized layer. The steps of agglomeration and granulation are well known to those skilled in the art and can be performed in various ways depending on the product properties to be achieved. Coating of particulate products such as powders, granules or tablets can be achieved by spraying a liquid on the fluidized particles under controlled conditions.

A composition having a low residual moisture content can therefore be obtained. A level of residual moisture content is achieved which offers long term preservation at greater than refrigeration temperatures e.g. within the range from 40° C. to 56° C. or more, or lower than refrigeration temperatures e.g. within the range from 0 to −70° C. or below. The dried composition may thus have residual moisture content of 10% or less, 5% or less, 2% or less or 1% or less by weight. Preferably the residual moisture content is 0.5% or more 1% or more. Typically a dried composition has residual moisture content of from 0.5 to 10% by weight and preferably from 1 to 5% by weight.

The composition can be obtained in a dry powder form. A cake resulting from e.g. freeze-drying can be milled into powder form. A solid composition according to the invention thus may take the form of free-flowing particles.

In the invention, a powder may be compressed into tablet form. Tablets are described above. The powder may also be filled into capsules. Once again, capsules are described above.

The following Example illustrates the invention.

EXAMPLES

Example 1

Two Adenovirus (human Adenovirus TypeS (dE1/E3)) constructs were prepared by standard molecular biological techniques. The first adenovirus carried a GIP (Glucose-dependent insulinotropic polypeptide) promoter driving INS (proinsulin) expression (designated GIP-INS). The sequences used were a 1.2 kb rat GIP insert as described in Biol Res 44: 301-305, 2011 and the NCBI Reference Sequences (proinsulin) NM 019129.2/3. The second adenovirus carried a "null" eGFP (720 bp, Gene. 1996; 173 (1 Spec No):33-8) construct (designated GIP-GFP), expressing enhanced green fluorescent protein. Expression of GFP was controlled using the same promoter system as for the insulin cassette.

High titre adenoviral stocks were prepared by virus culture in HEK 293 cells and subsequent purification by double caesium chloride density gradient centrifugation followed by column desalting (e.g. PD-10) into the following excipient formulation:
  N,N-Dimethylglycine (DMG) (0.2M);
  methylsulfonylmethane (MSM) (0.2M); and
  sucrose (0.4M).

The final excipient formulated adenovirus was freeze dried and the resultant cake was spatula powderized, then filled into Porcine Gelatin capsules size 9 (Torpac Inc. NJ, 07006). Finally, the capsules were coated by enteric coating methods know to those skilled in the art for targeted delivery to the duodenum (Poly (methacylic acid-co-ethyl acrylate) 1:1 copolymer).

In vivo assessment of the adenovirus excipient formulated capsules orally administered (by oral gavage) was performed in STZ (35 mg/Kg) induced high fat feed diabetic rats (Cardiovascular Diabetology 2013 12:136) with tail vein blood (plasma sample) glucose assessment pre (−3 days) and post dosing (day 3, 5, 8, 10, 12, and 15) with the corresponding dosing at day 1. Results are presented in FIG. 1. The respective oral dose adenovirus excipient formulated doses were titrated by TCID50, CPE assay in HEK293 cells, to quantity the live virus dose orally administered. These were: —GIP-INS at a 9.6E+07 TCID dose and GIP-GFP at a 1.6+07 TCID dose. In FIG. 1, the diabetic status of all rats dosed is indicated by the pre dosing (−3 days) blood glucose levels at approximately x4 normal levels (~7 mM).

Data were back-transformed adjusted means (n=5-6). SEMs were calculated from the residuals of the statistical model. Data were analysed by a general linear model with treatment as a factor and Day 1 body weight and log(Day −3) plasma glucose as covariates followed by Dunnett's test. Significant differences vs vehicle are donated with **$p<0.01$.

Example 2

An Adenovirus (human Adenovirus TypeS (dE1/E3)) construct was prepared by standard molecular biological techniques, composed of the CMV (cytomegalovirus) promoter driving BChE (Butyrylcholinesterase) expression designated Ad5-CMV-BChE. The NCBI Reference Sequences: —Butyrylcholinesterase NM_022942.1, rat species, was used.

Subsequently, high titre adenoviral stocks were prepared by virus culture in HEK 293 cells and subsequent purification by adenovirus chromatographically with final concentration into the DMG (0.2M)/MSM (0.2M)/Sucrose (0.4M) excipient formulation. The final excipient formulated adenovirus was freeze dried and the resultant cake was powderized, then hand filled into Porcine Gelatin capsules size 9 (Torpac Inc. NJ, 07006). Finally, the capsules were coated by enteric coating (Poly (methacylic acid-co-ethyl acrylate) 1:1 copolymer) for targeted delivery to the duodenum.

Figure 2:
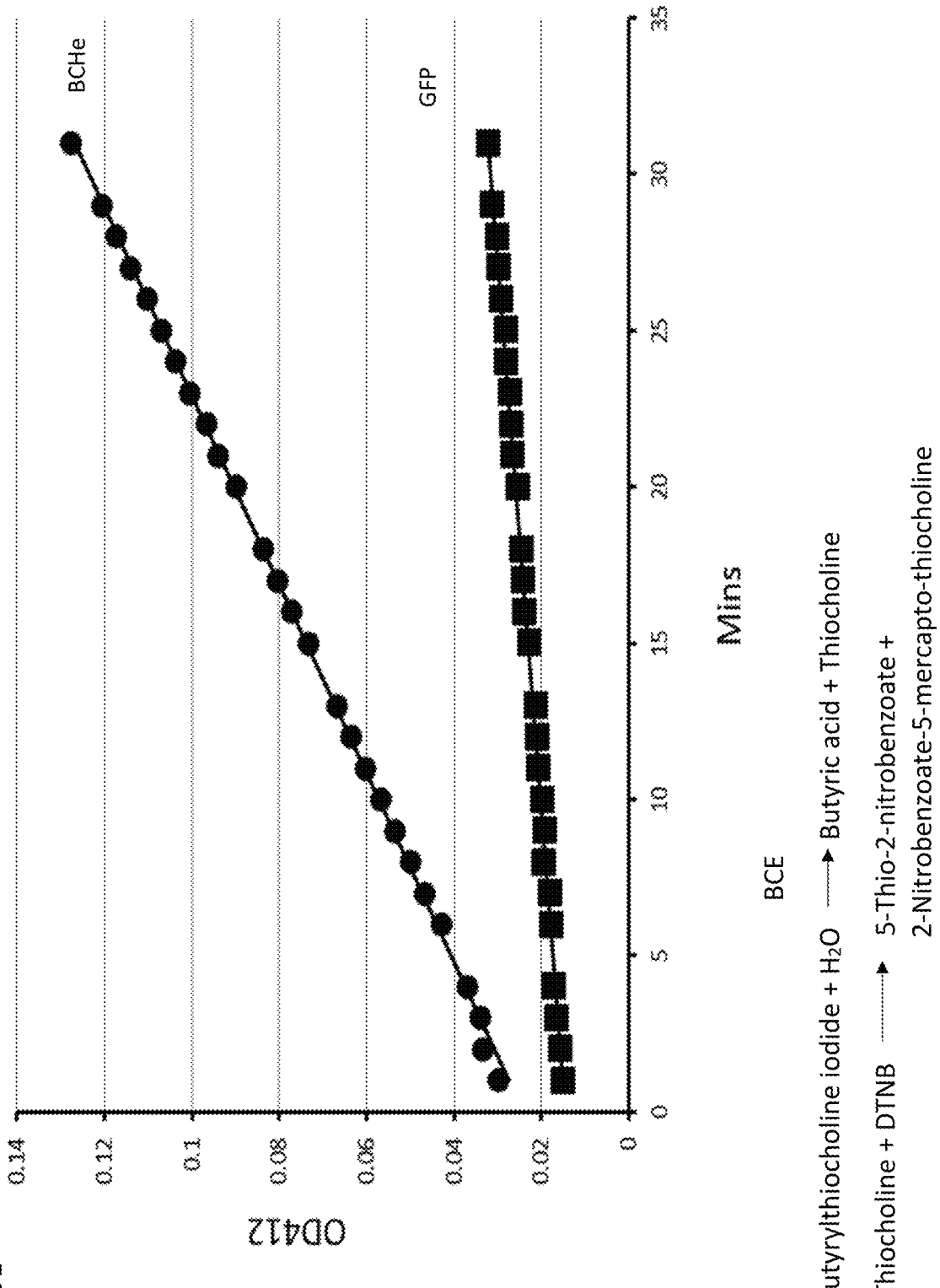
FIG. 2 shows that positive in-vitro Butyrylcholinesterase enzymatic activity was detected, butyrylthiocholine (BTC) iodide substrate, in cell culture (HEK293) supernatants following Ad5-CMV-BChE vector infection and essentially absent with nul Ad5-CMV-GFP vector (both non encapsulated).

Positive in-vitro Butyrylcholinesterase enzymatic activity was detected, butyrylthiocholine (BTC) iodide substrate, in cell culture (HEK293) supernatants following Ad5-CMV-BChE vector infection and essentially absent with nul Ad5-CMV-GFP vector (both non encapsulated). Results are shown in FIG. 2.

In vivo assessment of the andenovirus excipient formulated capsules orally administered was performed Brown Norway rats with tail vein blood (plasma sample) sampling (dosing day (pre dose), 1 d and 3 d post dosing), with the respective adenovirus excipient formulated dose level $2\times10^{\wedge}10$ vp/capsule determined spectrophotometrically (OD260 nm)

Figure 3:
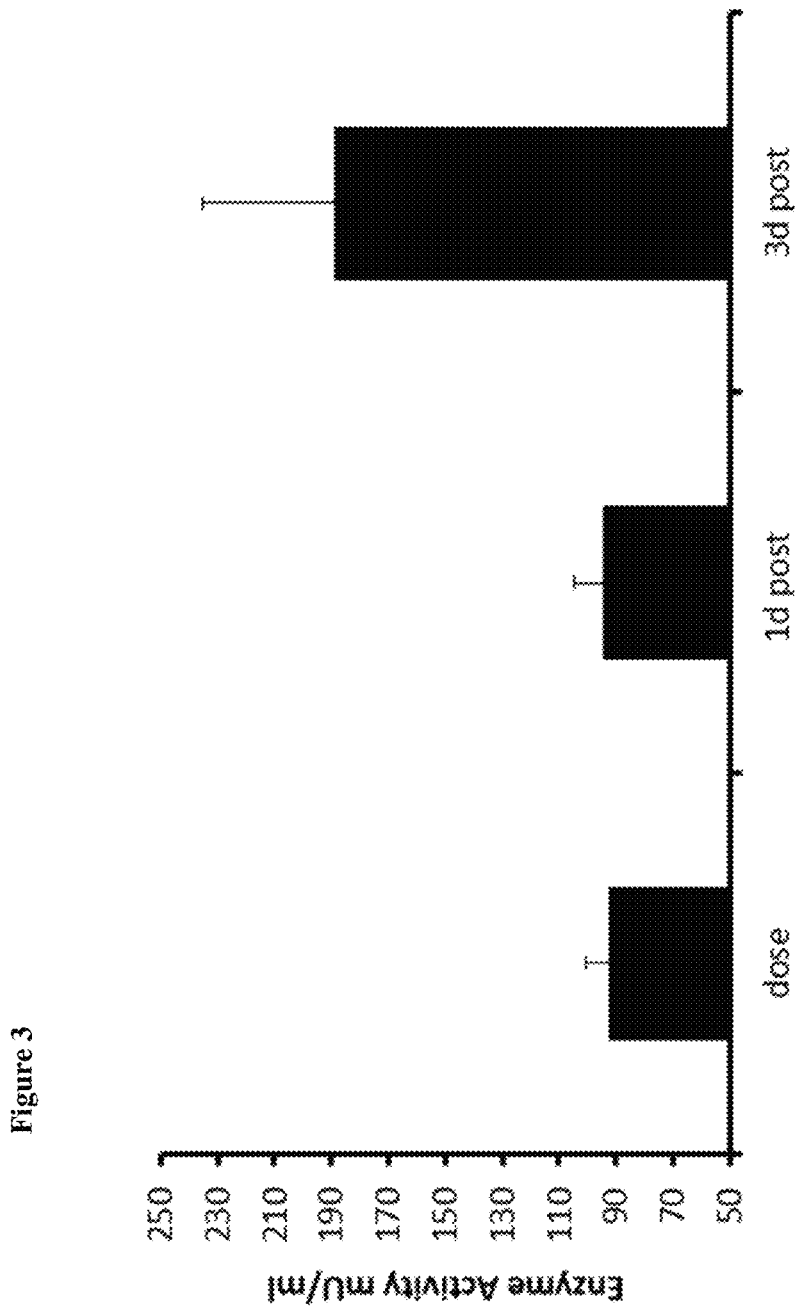
FIG. 3 shows the in vivo assessment of the adenovirus excipient formulated capsules orally administered to Brown Norway rats with tail vein blood (plasma sample) sampling (dosing day (pre dose), 1 d and 3 d post dosing), with the respective andenovirus excipient formulated dose level $2\times10"10$ vp/capsule determined spectrophotometrically (OD260 nm) BCHe levels in individual plasma samples, n=8 subjects, were measured by DetectX® Butyrylcholinesterase Fluorescent Activity Kit (K016-F1) and an elevated (P<0.01) enzyme activity level was detected 3 days after dosing.

BCHe levels in individual plasma samples, n=8 subjects, were measured by DetectX®Butyrylcholinesterase Fluorescent Activity Kit (K016-F1) and an elevated ($P<0.01$) enzyme activity level was detected 3 days after dosing. Results are presented in FIG. 3.

Example 3

An adenovirus (serotype 5) construct (dE1/E3)) was prepared composed of a CMV promoter driving Zika antigen (E and NS1) expression, designated Ad5_FP (E/NS1)_GW. High titre virus stocks were prepared by virus culture in HEK 293 cells, followed by formulation with excipients (0.4 M sucrose, 0.2 M DMG, 0.2 MSM) and freeze drying. The resultant cake, powder, was filled into Porcine Gelatin capsules followed by enteric coating to enhance lower GI delivery.

This product was tested in a 12 IFN$\alpha\beta^{-/-}$ mouse study (6 mice were treated with vaccine and 6 were treated with placebo). SV129 mice were also run as an immune-competent control for antibody production.

Mice were dosed by oral gavage at days 0, 14 and 28 followed by challenge with Zika virus (HS-2015-BA-01 isolate; $4\times10^5$ PFU administered intravenously in the tail vein at day 42). Bodyweight, intraocular pressure and brain viremia were measured.

Figure 4:
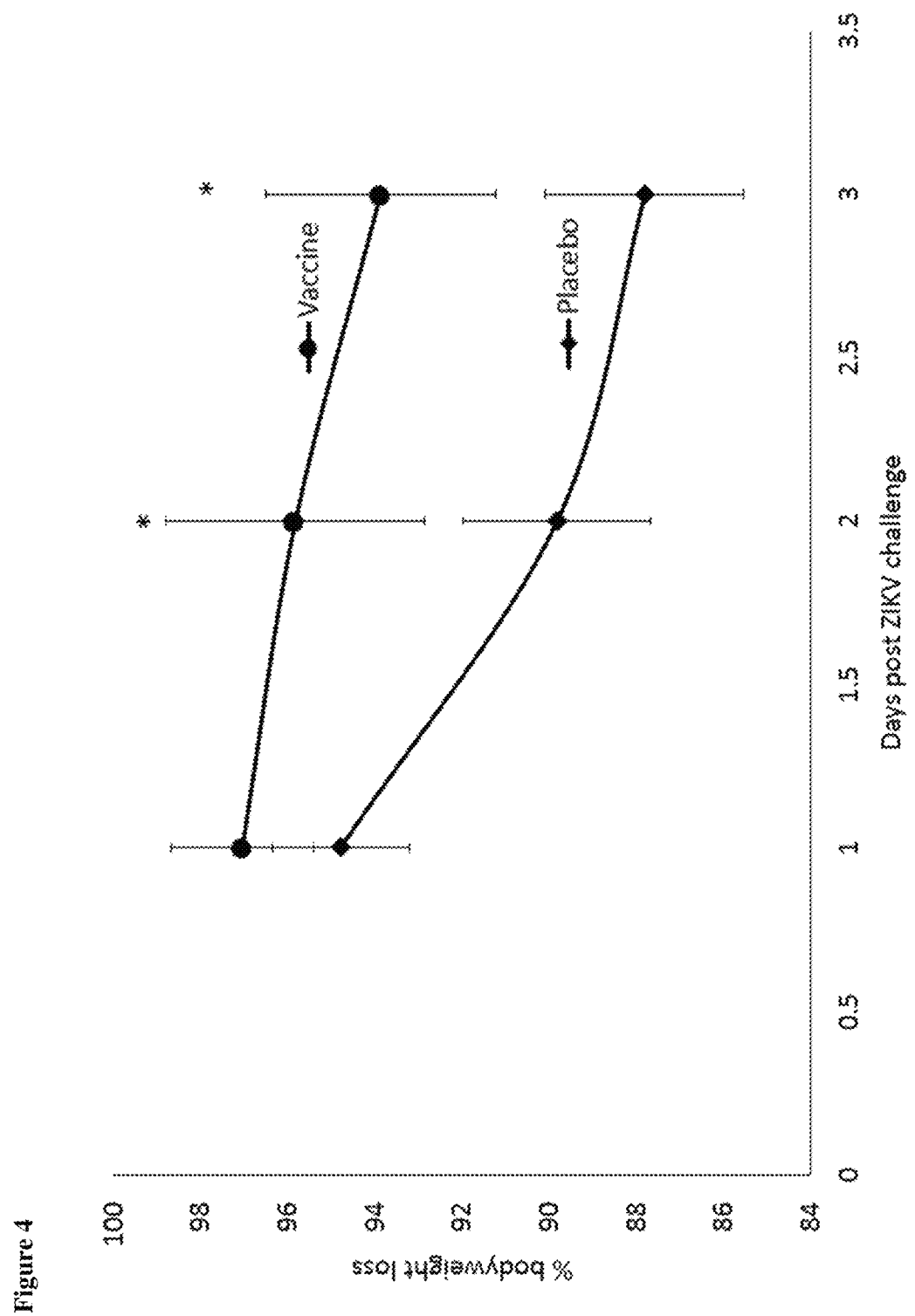
FIG. 4 shows the percentage of bodyweight loss in $IFN\alpha\beta^{-/-}$ mice upon challenge with Zika virus up to 3 days post-infection. Vaccinated mice showed a lesser degree of bodyweight loss compared with mice administered the placebo (p=0.0003).

FIG. 4 shows the percentage of bodyweight loss in mice administered the vaccine and mice administered placebo for 3 days after viral challenge (IFN$\alpha\beta^{-/-}$ mice are known to lose bodyweight on challenge with Zika virus). The vaccine afforded protection (p=0.0003).

Figure 5:
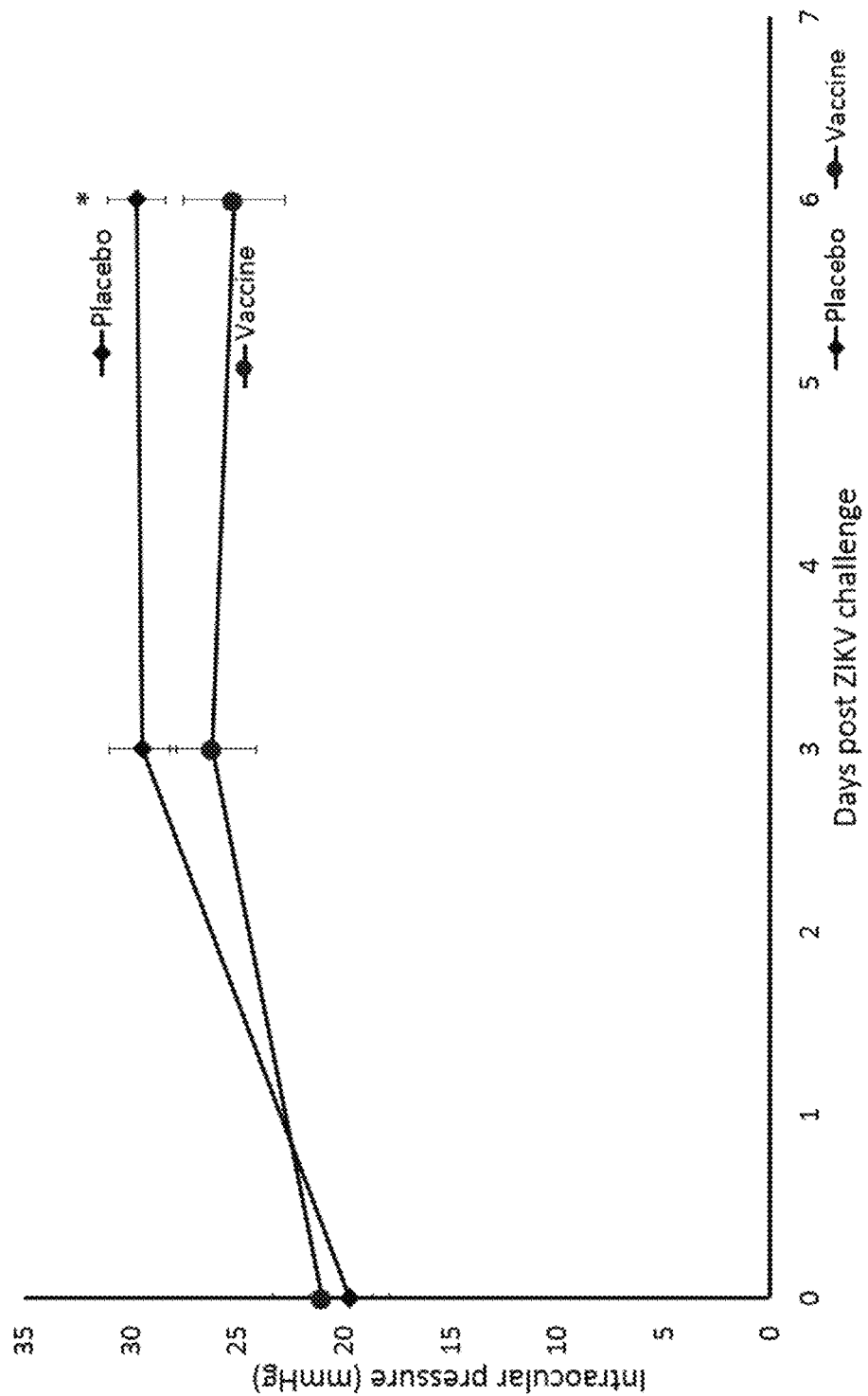
FIG. 5 shows the intraocular pressure in $IFN\alpha\beta^{-/-}$ mice upon challenge with Zika virus. Vaccinated mice were protected relative to placebo (p=0.016).

FIG. 5 shows the effects of viral challenge on intraocular pressure for vaccinated mice and mice administered placebo. Again, vaccination afforded protection (p=0.016)

Figure 6:
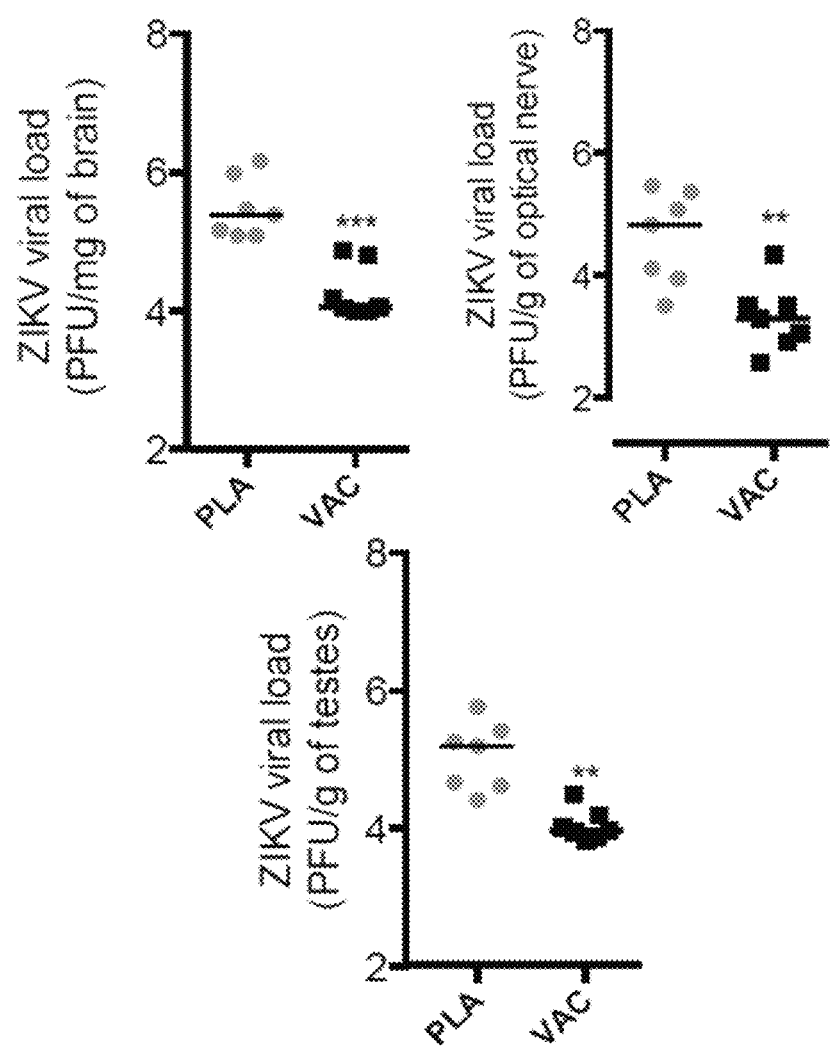
FIG. 6 shows viremia in mice after challenge with Zika virus. A reduction in viremia was observed following administration of 3 doses of vaccine (VAC). Results for placebo are presented as "PLA".
Figure 7:
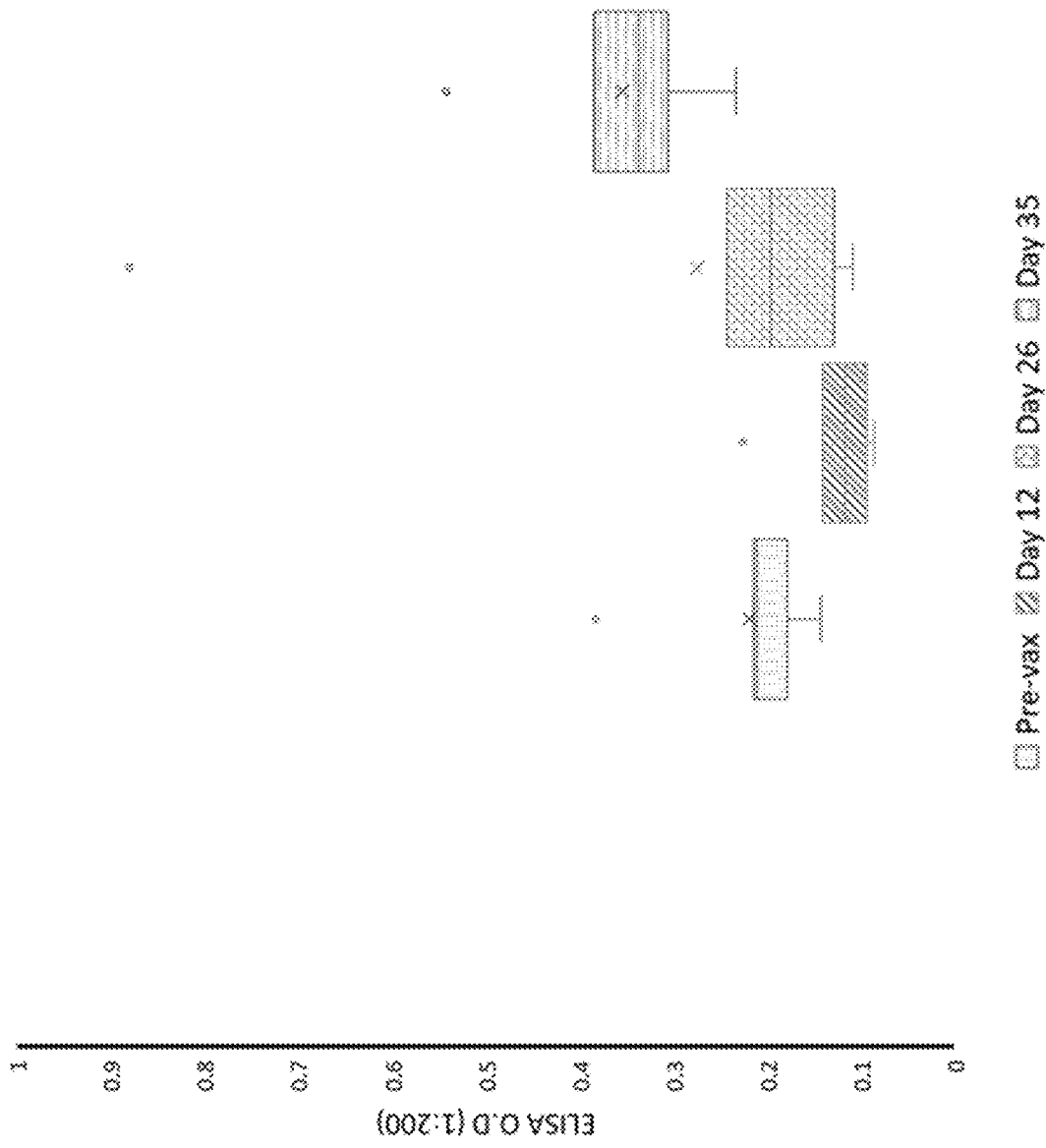
FIG. 7 shows the response of immune-competent mice to vaccine (control for antibody production).
Figure 7:
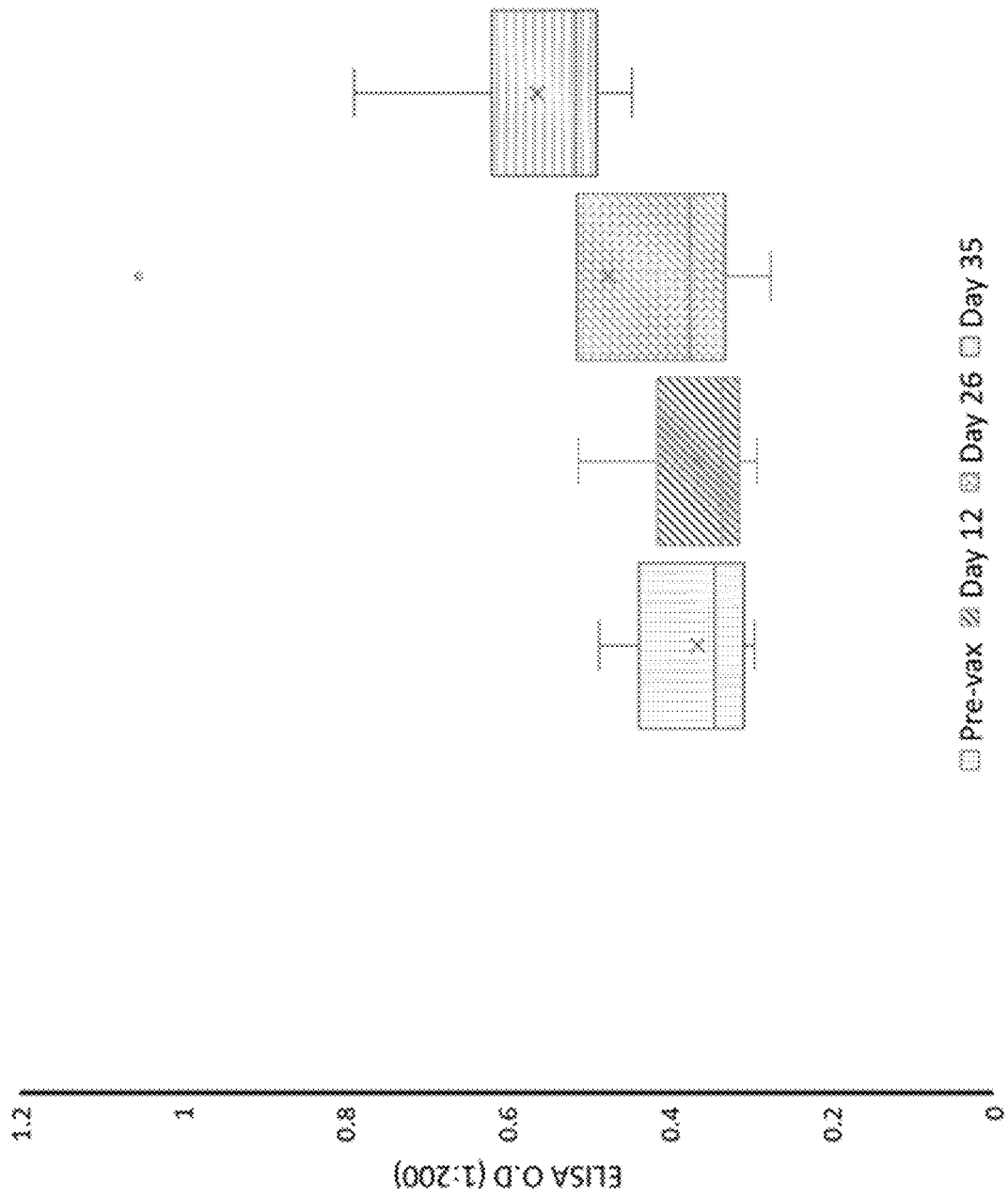

FIG. 6 then shows brain, optical nerve and testes viremia (recorded at day 49). Protective efficacy was observed by reduced viremia load with respect to the placebo control.

Example 4

Oral Zika vaccine was tested in Callithrix penicillata (2 pre-immune controls, 2 placebo and 2 vaccinated). Vaccine formulation was prepared as above and filled into enterically coated capsules ($2.1\times10^8$ TCID$_{50}$ vaccine and $2.5\times10^8$ TCID$_{50}$ placebo per dose). Capsules were stored at ambient temperature for approximately 1 month post manufacture. Capsules were administered twice, at days 0 and 13.

Animals were then challenged with the Zika virus HS-2015-BA-01 clinical isolate ($5\times10^5$ PFU, administered subcutaneously on day 27 (14 days after the last dose of vaccine). Post challenge blood collection was carried out on days 1, 3, 6, 9, 12 and saliva and urine was collected on days 3, 6, 9 and 12.

Figure 8:
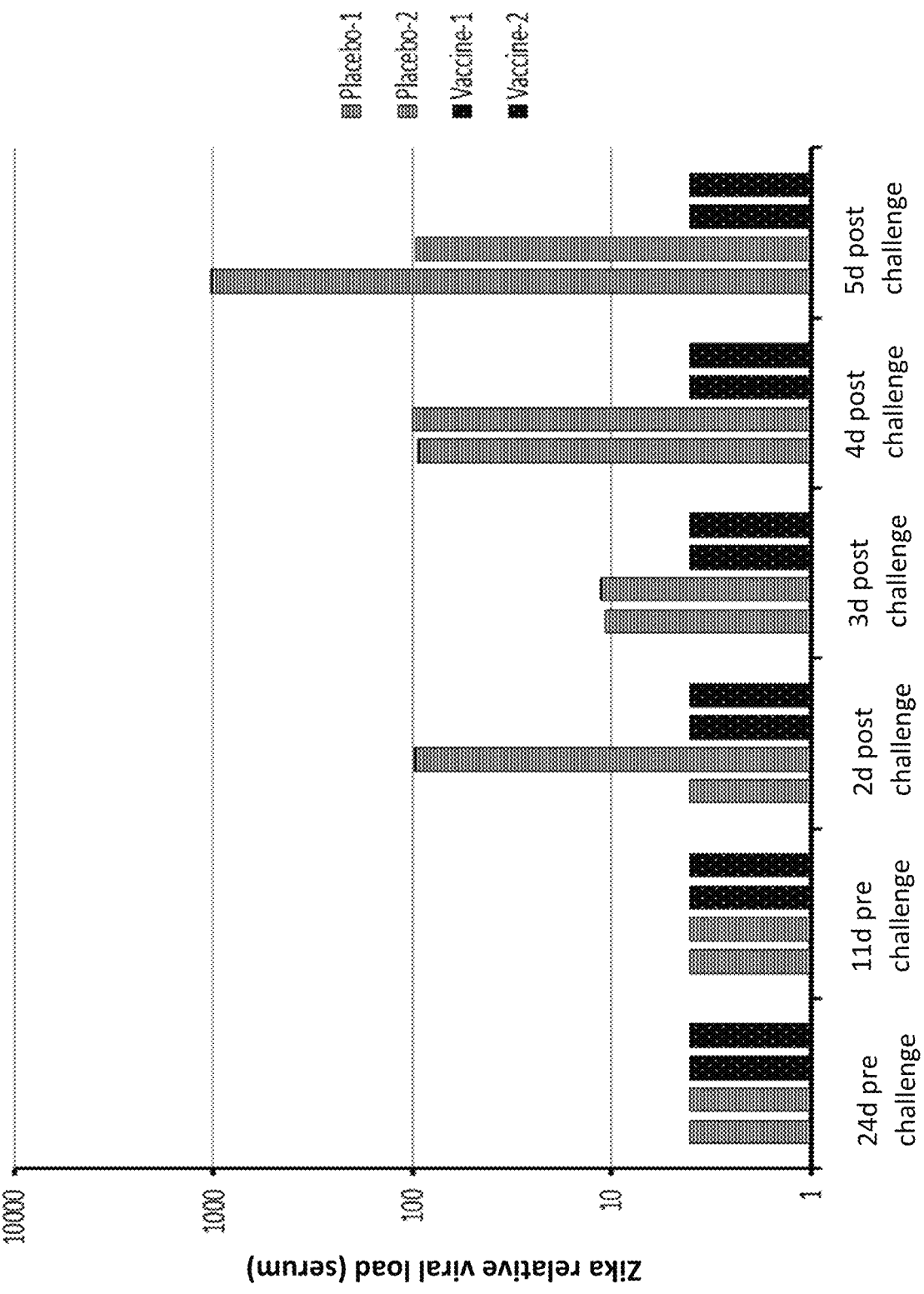
FIG. 8 shows a reduction in viremia in Callithrix penicillata following infectious Zika virus challenge with prior administration of 2 doses of oral capsules of vector.

FIG. 8 shows relative viral load up to 5 days post-challenge. The vaccine conferred immunity equivalent to prior exposure to Zika virus. No Zika virus was detected in the vaccinated or pre-immune groups (LOD=4). The vaccine was therefore efficacious after 1 month at ambient storage.

The invention claimed is:

1. A tablet or capsule for oral administration to a patient comprising adenoviral particles carrying a transgene, wherein the transgene encodes one or more antigens, and wherein the tablet or capsule is prepared by formulating the adenoviral particles comprising the transgene into a liquid composition which comprises:
    (a) sucrose at a concentration of 0.05 to 1 M;
    (b) N,N-dimethylglycine or a physiologically acceptable salt or ester thereof at a concentration of 0.07 to 1 M; and
    (c) dimethylsulfone at a concentration of 0.07 to 1 M; drying the liquid composition, and packaging the dried composition into the tablet or capsule, wherein the tablet or capsule is coated with an enteric coating.

2. The tablet or capsule according to claim 1, wherein the physiologically acceptable salt of N,N-dimethylglycine is a hydrochloride salt.

3. The tablet or capsule according to claim 1, wherein:
    (a) the liquid composition further comprises one or more other sugar(s) in addition to said sucrose;
    (b) the liquid composition further comprises one or more other sugar(s) in addition to said sucrose and the ratio of the concentration of said sucrose relative to the one or more other sugar(s) is from 1:1 to 20:1;
    (c) the liquid composition further comprises raffinose; or
    (d) the liquid composition comprises 0.2 M N,N-dimethylglycine, 0.2 M dimethylsulfone and 0.4 M sucrose.

4. The tablet or capsule according to claim 1, wherein:
    (a) the transgene encodes one or more Zika virus antigens;
    (b) the transgene encodes one or more Zika virus antigens derived from the envelope protein (E) and/or NS1;
    (c) the transgene encodes one or more HSV, optionally HSV2, antigens;
    (d) the transgene encodes one or more HSV antigens derived from glycoprotein C (gC), glycoprotein D (gD) and/or glycoprotein E (gE); or
    (e) expression of the transgene is controlled by a tissue-specific promoter.

5. A method of delivering a transgene(s) which encodes one or more antigens to target cells in a patient, said method comprising oral administration of a tablet or capsule comprising adenoviral particles which carry the transgene to the patient, wherein the tablet or capsule is prepared by formulating the adenoviral particles comprising the transgene into a liquid composition which comprises:
    (a) sucrose at a concentration of 0.05 to 1 M;
    (b) N,N-dimethylglycine or a physiologically acceptable salt or ester thereof at a concentration of 0.07 to 1 M; and
    (c) dimethylsulfone at a concentration of 0.07 to 1 M; drying the liquid composition, and packaging the dried composition into the tablet or capsule, wherein the tablet or capsule is enterically coated.

6. The method according to claim 5, wherein:
    (a) the transgene encodes one or more Zika virus antigens;
    (b) the transgene encodes one or more Zika virus antigens and the Zika virus antigen(s) is/are derived from the envelope protein (E) and/or NS1;
    (c) the transgene encodes one or more Herpes Simplex Virus (HSV), optionally HSV2, antigens; or
    (d) the transgene encodes one or more Herpes Simplex Virus (HSV) antigens and the HSV antigen(s) is/are derived from glycoprotein C (gC), glycoprotein D (gD), and/or glycoprotein E (gE).

7. The method according to claim 5, wherein expression of the transgene is controlled by a tissue-specific promoter.

8. The method according to claim 5, wherein: the physiologically acceptable salt of N,N-dimethylglycine is a hydrochloride salt.

9. The method according to claim 5, wherein:
    (a) the liquid composition further comprises one or more other sugar(s) in addition to said sucrose;
    (b) the liquid composition further comprises one or more other sugar(s) in addition to said sucrose and the ratio of the concentration of said sucrose relative to the one or more other sugar(s) is from 1:1 to 20:1;
    (c) the liquid composition further comprises raffinose;
    (d) the liquid composition comprises 0.2 M N,N-dimethylglycine, 0.2 M dimethylsulfone and 0.4 M sucrose.

10. A method of preparing adenoviral particles carrying a transgene which encodes one or more antigens for oral administration to a patient, said method comprising:
    (a) culturing and purifying adenoviral particles carrying the transgene;
    (b) formulating the viral particles in a pharmaceutical liquid composition which comprises
        (i) sucrose at a concentration of 0.05 to 1 M;
        (ii) N,N-dimethylglycine or a physiologically acceptable salt or ester thereof at a concentration of 0.07 to 1 M; and
        (iii) dimethylsulfone at a concentration of 0.07 to 1 M;
    (c) drying the liquid composition; and
    (d) packaging the dried composition into tablets or capsules for oral administration to the patient, wherein the tablets or capsules are coated with an enteric coating.

11. The method according to claim 10, wherein:
    (a) the physiologically acceptable salt of N,N-dimethylglycine is a hydrochloride salt;
    (b) the liquid composition further comprises one or more sugar(s) in addition to said sucrose;
    (c) the liquid composition further comprises one or more other sugar(s) in addition to said sucrose and the ratio of the concentration of sucrose relative to the one or more other sugar(s) is from 1:1 to 20:1;
    (d) the liquid composition further comprises raffinose; or
    (e) the viral particles are formulated in a liquid composition which comprises the viral particles, 0.2 M N,N-dimethylglycine, 0.2 M dimethylsulfone and 0.4 M sucrose.

12. The method according to claim 10, wherein:
    (a) the transgene encodes one or more Zika virus antigens;
    (b) the transgene encodes one or more Zika virus antigens derived from the envelope protein (E) and/or NS1;
    (c) the transgene encodes one or more HSV, optionally HSV2, antigens;
    (d) the transgene encodes one or more HSV antigens derived from glycoprotein C (gC), glycoprotein D (gD) and/or glycoprotein E (gE); or
    (e) expression of the transgene is controlled by a tissue-specific promoter.

* * * * *